(12) United States Patent
Lentz

(10) Patent No.: US 7,854,717 B1
(45) Date of Patent: *Dec. 21, 2010

(54) METHOD AND COMPOSITIONS FOR TREATMENT OF CANCERS

(75) Inventor: M. Rigdon Lentz, Brentwood, TN (US)

(73) Assignee: Biopheresis Technologies, Inc., Apex, NC (US)

( * ) Notice: Subject to any disclaimer, the term of this patent is extended or adjusted under 35 U.S.C. 154(b) by 1993 days.

This patent is subject to a terminal disclaimer.

(21) Appl. No.: 09/699,003

(22) Filed: Oct. 26, 2000

Related U.S. Application Data

(63) Continuation of application No. 09/316,226, filed on May 21, 1999, now Pat. No. 6,231,536, which is a continuation-in-part of application No. 09/083,307, filed on May 22, 1998, now Pat. No. 6,620,382.

(51) Int. Cl.
*A61M 37/00* (2006.01)
*C02F 1/00* (2006.01)
*B01D 37/00* (2006.01)
*A61K 45/00* (2006.01)
*A61K 39/395* (2006.01)

(52) U.S. Cl. .......... 604/5.01; 604/4.01; 604/8; 604/6.01; 210/638; 210/645; 210/767; 424/85.1; 424/145.1; 128/898

(58) Field of Classification Search .......... 604/4.01, 604/5.01–5.04, 6.01, 6.04; 128/898; 210/638, 210/645–46, 650–51, 767, 252; 424/9.1, 424/484, 486, 489–91, 78.08, 78.1, 85.1–85.2, 424/85.4, 85.5, 85.7, 130.1, 133.1, 134.1, 424/140.1, 141.1, 148.1, 145.1, 177.1, 529, 424/530; 435/2, 7.1, 7.2; 436/501, 503, 436/506, 507, 518, 536, 538, 64, 81, 813; 530/380, 386, 387.1–387.15, 388.21–388.23, 530/412–13, 415, 810–12, 817, 827–30, 530/860–866, 387.7, 388.2, 388.7, 389.6
See application file for complete search history.

(56) References Cited

U.S. PATENT DOCUMENTS 4,116,589 A 9/1978 Rishton
(Continued)

FOREIGN PATENT DOCUMENTS

CA 2107340 12/1992
(Continued)

OTHER PUBLICATIONS

Lentz, "Continuous Whole Blood UltraPheresis Procedure in Patients with Metastatic Cancer", Journal of Biological Response Modifiers 8(5):511-527 (1989).*

(Continued)

*Primary Examiner*—Patricia Bianco
(74) *Attorney, Agent, or Firm*—Clark & Elbing LLP

(57) ABSTRACT

A method to treat cancer uses ultrapheresis, refined to remove compounds of less than 120,000 daltons molecular weight, followed by administration of replacement fluid, to stimulate the patient's immune system to attack solid tumors. In the preferred embodiment, the patient is ultrapheresed using a capillary tube ultrafilter having a pore size of 0.02 to 0.05 microns, with a molecular weight cutoff of 120,000 daltons, sufficient to filter one blood volume. The preferred replacement fluid is ultrapheresed normal plasma. The patient is preferably treated daily for three weeks, diagnostic tests conducted to verify that there has been shrinkage of the tumors, then the treatment regime is repeated. The treatment is preferably combined with an alternative therapy, for example, treatment with an anti-angiogenic compound, one or more cytokines such as TNF, gamma interferon, or IL-2, or a procoagulant compound. The treatment increases endogenous, local levels of cytokines, such as TNF. This provides a basis for an improved effect when combined with any treatment that enhances cytokine activity against the tumors, for example, treatments using alkylating agents, doxyrubicin, carboplatinum, cistplatimum, and taxol. Alternatively, the ultrapheresis treatment can be combined with local chemotherapy, systemic chemotherapy, and/or radiation.

15 Claims, 2 Drawing Sheets

U.S. PATENT DOCUMENTS

| | | | |
|---|---|---|---|
| 4,189,470 A | 2/1980 | Rose | |
| 4,191,182 A | 3/1980 | Popovich et al. | |
| 4,350,156 A | 9/1982 | Malchesky et al. | |
| 4,362,155 A | 12/1982 | Skurkovich | |
| 4,375,414 A | 3/1983 | Strahilevitz | |
| 4,439,332 A | 3/1984 | Frank | |
| RE31,688 E | 9/1984 | Popovich et al. | |
| 4,486,282 A | 12/1984 | Bier | |
| 4,512,763 A | 4/1985 | Schneider | |
| 4,581,010 A | 4/1986 | Skurkovich et al. | |
| 4,605,394 A | 8/1986 | Skurkovich | |
| 4,614,513 A | 9/1986 | Bensinger | |
| 4,620,977 A | 11/1986 | Strahilevitz | |
| 4,633,417 A | 12/1986 | Wilburn et al. | |
| 4,634,417 A | 1/1987 | Korec | |
| 4,664,913 A | 5/1987 | Mielke et al. | |
| 4,708,713 A * | 11/1987 | Lentz | 604/5.02 |
| 4,787,974 A | 11/1988 | Ambrus et al. | |
| 4,801,449 A | 1/1989 | Balint, Jr. et al. | |
| 4,813,924 A | 3/1989 | Strahilevitz | |
| 4,824,432 A | 4/1989 | Skurkovich et al. | |
| 4,834,973 A | 5/1989 | Strahilevitz | |
| 4,863,611 A | 9/1989 | Bernstein | |
| 4,865,841 A | 9/1989 | Balint, Jr. et al. | |
| 4,963,265 A | 10/1990 | Okarma et al. | |
| 5,037,645 A | 8/1991 | Strahilevitz | |
| 5,037,649 A | 8/1991 | Balint, Jr. et al. | |
| 5,078,673 A | 1/1992 | Abrams | |
| 5,135,919 A | 8/1992 | Folkman et al. | |
| 5,147,638 A | 9/1992 | Esmon et al. | |
| 5,290,807 A | 3/1994 | Folkman et al. | |
| 5,340,736 A | 8/1994 | Goldberg et al. | |
| 5,356,374 A | 10/1994 | Hogan et al. | |
| 5,359,037 A | 10/1994 | Wallach | |
| 5,403,917 A | 4/1995 | Boos et al. | |
| 5,523,096 A * | 6/1996 | Okarma et al. | 424/489 |
| 5,565,332 A | 10/1996 | Hoogenboom et al. | |
| 5,597,899 A | 1/1997 | Banner et al. | |
| 5,605,690 A | 2/1997 | Jacobs et al. | |
| 5,610,279 A | 3/1997 | Brockhaus | |
| 5,621,077 A | 4/1997 | Novick et al. | |
| 5,626,843 A | 5/1997 | Skurkovich et al. | |
| 5,629,327 A | 5/1997 | D'Amato | |
| 5,639,725 A | 6/1997 | O'Reilly et al. | |
| 5,643,732 A | 7/1997 | Strahilevitz | |
| 5,679,260 A | 10/1997 | Boos et al. | |
| 5,698,586 A | 12/1997 | Kishimoto et al. | |
| 5,705,615 A | 1/1998 | Lim et al. | |
| 5,712,291 A | 1/1998 | D'Amato | |
| 5,713,491 A | 2/1998 | Hughes et al. | |
| 5,716,981 A | 2/1998 | Hunter et al. | |
| 5,730,713 A | 3/1998 | Okarma et al. | |
| 5,733,876 A | 3/1998 | O'Reilly et al. | |
| 5,736,138 A | 4/1998 | Pfizenmaier et al. | |
| 5,753,227 A | 5/1998 | Strahilevitz | |
| 5,792,845 A | 8/1998 | O'Reilly et al. | |
| 5,808,029 A | 9/1998 | Brockhaus | |
| 5,817,522 A | 10/1998 | Goodman et al. | |
| 5,817,528 A * | 10/1998 | Bohm et al. | 436/529 |
| 5,840,588 A | 11/1998 | Strahilevitz | |
| 5,861,483 A * | 1/1999 | Wolpe | 530/385 |
| 5,869,047 A | 2/1999 | Blake | |
| 5,888,511 A | 3/1999 | Skurkovich et al. | |
| 5,910,252 A | 6/1999 | Truitt et al. | |
| 5,919,898 A * | 7/1999 | Nakatani et al. | 530/345 |
| 5,925,633 A | 7/1999 | Singh et al. | |
| 5,932,704 A | 8/1999 | Jubinsky | |
| 5,965,394 A | 10/1999 | Bandman et al. | |
| 5,980,887 A | 11/1999 | Isner et al. | |
| 6,017,527 A * | 1/2000 | Maraskovsky et al. | 424/93.71 |
| 6,039,946 A | 3/2000 | Strahilevitz | |
| RE36,755 E | 6/2000 | Smith et al. | |
| 6,133,431 A | 10/2000 | Yasuda | |
| 6,197,289 B1 | 3/2001 | Wirt et al. | |
| 6,221,614 B1 | 4/2001 | Prusiner et al. | |
| 6,231,536 B1 * | 5/2001 | Lentz | 604/5.04 |
| 6,232,446 B1 | 5/2001 | Wallach | |
| 6,245,038 B1 | 6/2001 | Borberg et al. | |
| 6,262,127 B1 | 7/2001 | Acemoglu et al. | |
| 6,264,623 B1 | 7/2001 | Strahilevitz | |
| 6,287,516 B1 | 9/2001 | Matson et al. | |
| 6,379,708 B1 * | 4/2002 | Howell et al. | 424/529 |
| 6,428,790 B1 | 8/2002 | Boyd | |
| 6,432,405 B1 | 8/2002 | Weinberg et al. | |
| 6,528,057 B1 | 3/2003 | Ambrus et al. | |
| 6,561,997 B1 | 5/2003 | Weitzel et al. | |
| 6,569,112 B2 | 5/2003 | Strahilevitz | |
| 6,602,502 B1 | 8/2003 | Strahilevitz | |
| 6,602,993 B2 | 8/2003 | Wallach et al. | |
| 6,607,501 B2 | 8/2003 | Gorsuch | |
| 6,607,723 B1 | 8/2003 | Good et al. | |
| 6,620,382 B1 * | 9/2003 | Lentz | 422/44 |
| 6,627,151 B1 | 9/2003 | Borberg et al. | |
| 6,630,315 B1 | 10/2003 | Miwa et al. | |
| 6,676,622 B2 | 1/2004 | Strahilevitz | |
| 6,685,664 B2 | 2/2004 | Levin et al. | |
| 6,720,155 B1 | 4/2004 | Lopez et al. | |
| 6,774,102 B1 | 8/2004 | Bell et al. | |
| 6,824,986 B1 | 11/2004 | Finkelman et al. | |
| 6,866,846 B1 | 3/2005 | Heinrich et al. | |
| 6,878,127 B2 | 4/2005 | Brady et al. | |
| 6,982,089 B2 | 1/2006 | Tobinick | |
| 7,105,484 B2 | 9/2006 | Klein et al. | |
| 7,196,070 B2 | 3/2007 | Sukumar | |
| 7,238,776 B2 | 7/2007 | Hauptmann | |
| 7,368,295 B2 | 5/2008 | Tovar et al. | |
| 2001/0010818 A1 | 8/2001 | Engle et al. | |
| 2001/0039392 A1 | 11/2001 | Strahilevitz | |
| 2002/0019603 A1 | 2/2002 | Strahilevitz | |
| 2002/0058031 A1 | 5/2002 | Tung et al. | |
| 2002/0086276 A1 | 7/2002 | Srivastava | |
| 2002/0107469 A1 | 8/2002 | Bolan et al. | |
| 2002/0111577 A1 | 8/2002 | Sirimanne et al. | |
| 2002/0114728 A1 | 8/2002 | Kulish et al. | |
| 2002/0119147 A1 | 8/2002 | Howell et al. | |
| 2002/0159995 A1 | 10/2002 | Brady et al. | |
| 2002/0183677 A1 | 12/2002 | Chang et al. | |
| 2002/0187069 A1 | 12/2002 | Levin et al. | |
| 2002/0197249 A1 | 12/2002 | Brady et al. | |
| 2002/0197250 A1 | 12/2002 | Brady et al. | |
| 2002/0197251 A1 | 12/2002 | Brady et al. | |
| 2003/0073822 A1 | 4/2003 | Lofling et al. | |
| 2003/0115854 A1 | 6/2003 | Glenn et al. | |
| 2003/0125657 A1 | 7/2003 | Koll et al. | |
| 2003/0127390 A1 | 7/2003 | Davis, Jr. | |
| 2003/0129130 A1 | 7/2003 | Guire et al. | |
| 2003/0133929 A1 | 7/2003 | Cham | |
| 2003/0138349 A1 | 7/2003 | Robinson et al. | |
| 2003/0148404 A1 | 8/2003 | Michaelson | |
| 2003/0163077 A1 | 8/2003 | Kim et al. | |
| 2003/0195452 A1 | 10/2003 | Hunley et al. | |
| 2003/0215443 A1 | 11/2003 | Coffey et al. | |
| 2004/0044301 A1 | 3/2004 | Levin et al. | |
| 2004/0054315 A1 | 3/2004 | Levin et al. | |
| 2005/0244371 A1* | 11/2005 | Lentz | 424/85.1 |
| 2005/0265996 A1 | 12/2005 | Lentz | |
| 2007/0065514 A1 | 3/2007 | Howell et al. | |
| 2008/0057060 A1 | 3/2008 | Lentz | |
| 2008/0075690 A1 | 3/2008 | Howell et al. | |
| 2008/0145333 A1 | 6/2008 | Lentz | |

| | | |
|---|---|---|
| 2008/0275376 A1 | 11/2008 | Howell et al. |

FOREIGN PATENT DOCUMENTS

| | | |
|---|---|---|
| DE | 3302384 | 1/1983 |
| DE | 43 45 200 A1 | 12/1994 |
| DE | 196 24 250 A1 | 1/1998 |
| EP | 0 184 040 | 6/1986 |
| EP | 0076665 | 1/1987 |
| EP | 289896 | 7/1992 |
| EP | 334165 | 12/1995 |
| EP | 787500 | 12/1999 |
| EP | 589982 | 1/2001 |
| GB | 2136314 | 9/1984 |
| JP | 56092824 | 7/1981 |
| JP | 02045064 | 2/1990 |
| JP | 6 296860 | 10/1994 |
| RU | 2 130 069 | 5/1999 |
| WO | WO 79/01121 | 12/1979 |
| WO | WO 90/009798 | 9/1990 |
| WO | WO 9100742 | 1/1991 |
| WO | WO 91/09967 | 7/1991 |
| WO | WO 93/012142 | 6/1993 |
| WO | WO 94/009137 | 4/1994 |
| WO | WO 94/026924 | 11/1994 |
| WO | WO 96/16666 | 6/1996 |
| WO | WO 97/14964 | 4/1997 |
| WO | WO 98/17799 | 4/1998 |
| WO | WO 98/28001 | 7/1998 |
| WO | WO 99/61085 A | 12/1999 |
| WO | WO 01/37873 | 5/2001 |
| WO | WO 03/056896 | 7/2003 |
| WO | WO 05/037865 | 4/2005 |
| WO | WO 06/002151 | 1/2006 |
| WO | WO 08/115597 | 1/2006 |

OTHER PUBLICATIONS

Selinsky et al., "Multifaceted inhibition of anti-tumor immune mechanism by soluble tumour necrosis factor receptor type I", Immunology 94(1):88-93 (1998).*

Selinsky et al. ("Multifaceted inhibition of anti-tumor immune mechanism by soluble tumour necrosis factor receptor type I").*

Feinman et al. (Tumor Necrosis Factor Is An Important Mediator of Tumor Cell Killing By Human Monocytes).*

Van Zee et al. (Tumor necrosis factor soluble receptors circulate during experimental and clinical inflammation and can protect against excessive tumor necrosis factor I in vitro and in vivo).*

Andrews, et al., "Characterization of the receptor for tumor necrosis factor (TNF) and lymphotoxin LT) on human T lymphocytes: TNF and LT differ in their receptor binding properties and the induction of MHC class I proteins on a human CD4$^+$ T cell hybridoma," *J Immunol* 144(7):2582-91 (1990).

Bonavida, et al., (eds), Tumor Necrosis Factor/Cachecin and Related Cytokines. Int. Conf. Tumor Necrosis Factor and Related Cytotoxins, Heidelberg, 1987, pp. 7-19 (Karger, Basel1988).

Chen, et al., "Soluble TNF- Receptors are constitutively shed and downregulate adhesion molecule expression in malignant gliomas," *J. Neuropathol. Exp. Neurol.* 56(5):541-550 (1997).

Feinman, et al., "Tumor necrosis factor is a important mediator of tumor cell killing by human monocytes," *J Immunol* 138(2):635-40 (1987).

Gatanaga, et al., "Identification of TNF-LT blocking factor(s) in the serum and ultrafiltrates of human cancer patients," *Lymphokine Res* 9(2):225-29 (1990).

Haranaka & Satomi, "Cytotoxic activity of tumor necrosis factor (TNF) on human cancer cells in vitro," *Jpn J Exp Med* 51(3):191-94 (1981).

Howard, et al., Vaccinia virus homologues of the Shope fibroma inverted terminal repeat proteins and a discontinuous ORF related to the tumor necrosis factor receptor family, *Virology* 180(2):633-47 (1991).

Langkopf & Atzpodien, "Soluble tumor necrosis factor receptors as prognostic factors in cancer patients," *Lancet* 344(8914):57-58 (1994).

Mathias, et al., "Activation of the Sphingomyelin signaling pathway intact EL4 cells and in a cell-free system by IL-I," *Science* 259:519-22 (1993).

Philip & Epstein, "Tumor necrosis factor as immunomodulator and mediator monocyte cytotoxicity induced by itself, Gamma-interferon and Interleukin-1," *Nature* 323(6083):86-87 (1986).

Urban, et al., "Tumor necrosis factor: A potent effector molecule for tumor cell killing by activated macrophages," *Proc Natl Acad Sce USA* 83:5233-37 (1986).

Ziegler-Heitbrock, et al., "Tumor necrosis factor as effector molecule in monocyte-mediated cytotoxicity," *Cancer Res* 46:5947-52 (1986).

Gatanaga, et al., "Purification and characterization of an inhibitor (soluble tumor necrosis factor receptor) for tumor necrosis and lymphotoxin obtained from the serum ultrafiltrates of human cancer patients," *Proceedings of the National Academy of the USA* 87(22):8781-87814 (1990).

Lentz, "Continuous whole blood UltraPheresis procedure in patients with metastatic cancer," *Journal of Biological Response Modifiers* 8(5):511-527 (1989).

Lentz, "The role of therapeutic apheresis in the treatment of cancer: a review," *Therapeutic Apheresis* 3(1):40-49 (1999).

Selinsky, et al., "Multifaceted inhibition of anti-tumor immune mechanisms by soluble tumour necrosis factor receptor type-1," *Immunology* 94(1):88-93 (1998).

Tetta, et al., "Continuous plasma filtration coupled with sorbents," *Kidney International* 53(66):S186-S189 (1998).

Aderka, et al., "Increased serum levels of soluble receptors for tumor necrosis factor in cancer patients," *Cancer Res.* 51: 5602-5607 (1991).

Amit, et al., "Three-dimensional structure of an antigen-antibody complex at 2.8 resolution," *Science* 233: 747-751 (1986).

Clackson, et al., "Making of antibody fragments using phage display libraries," *Nature* 352: 624-688 (1991).

Daugherty, et al., "Polymerase chain reaction facilitates the cloning, CDR-grating, and rapid expression of a murine monoclonal antibody directed against the CD18 component of leukocyte integrins," *Nucl. Acids Res.* 19: 2471-2476 (1991).

Digel, et al., "High levels of circulating soluble receptors for tumor necrosis factor in hairy cell leukemia and type B chronic lymphocytic leukemia," *J. Clin. Invest.* 89: 1690-1693 (1992).

Elsasser-Beile, et al., "Increased plasma concentrations for type I and II tumor necrosis factor receptors and IL-2 receptors in cancer patients," *Tumor Biol.* 15: 17-24 (1993).

Ey, et al., "Isolation of pure $IgG_1$, $IgG_{2a}$, and $IgG_{2b}$ immunoglobins from mouse serum using protein A-Sepharose," *Immunochemistry* 15:429-436 (1978).

Kabat, et al., eds., *Sequences of Proteins of Immunological Interest*, 4$^{th}$ ed., U.S Dept. Health & Human Services: Bethesda, MD (1987).

Kessler, "Adsorptive plasma treatment: optimization of extracorporeal devices and systems," *Blood Purif.* 11: 150-157 (1993).

Lentz, et al., "Low molecular weight protein apheresis and regression of breast cancer," *Jpn. J. Apheresis* 16(1): 107-114 (1997).

Panka, et al., "Variable region framework differences result in decreased or increased affinity of variant anti-digoxin antibodies," *Proc. Natl. Acad. Sci. USA* 85: 3080-3084 (1988).

Rudikoff, et al., "Single amino acid substitution altering antigen-binding specificity," *Immunology* 79: 1979-1983 (1982).

Selinsky & Howell, "Soluble tumor necrosis factor receptor type I enhances tumor development and persistence in vivo," *Cell. Immunol.* 200: 81-87 (2000).

Selinsky, "Dissertation: The role of soluble tumor necrosis factor type I in tumor survival," Colorado State University, Fort Collins, Colorado (1999).

Gerain, et al., "Systemic release of soluble TNF receptors after high-dose TNF in isolated limb perfusion" *Cytokine* 9(12):1034-1042 (1997).

Abbruzzese, et al., "A phase II trial of recombinant human interferon-gamma and recombinant tumor necrosis factor in patients with advanced gastrointestinal malignancies: Results of a trial terminated by excessive toxicity" *Journal of Biological Response Modifiers* 9:522-527 (1990).

Adolf and Apfler, "A monoclonal antibody-based enzyme immunoassay for quantitation of human tumor necrosis factor binding protein I, a soluble fragment of the 60kDa TNF receptor, in biological fluids" *J. Immunol. Meth.* 143:127-136 (1991).

Ajani, et al., "Phase I and II studies of the combination of recombinant human interferon-γ and 5-fluorouracil in patients with advanced colorectal carcinoma" *Journal of Biological Response Modifiers* 8:140-146 (1989).

Albertini, et al., "Limiting dilution analysis of lymphokine-activated killer cell precursor frequencies in peripheral blood lymphocytes of cancer patients receiving interleukin-2 therapy" *Journal of Biological Response Modifiers* 9:456-462 (1990).

Arend, "Inhibiting the effects of cytokines in human diseases" *Adv. Int. Med.* 40:365-394 (1995).

Avner, et al., "Therapeutic murine monoclonal antibodies developed for individuals cancer patients" *Journal of Biological Response Modifiers* 8:25-36 (1989).

Balcewicz-Sablinska, et al., "Pathogenic Mycobacterium tuberculosis evades apoptosis of host macrophages by release of TNF-R2, resulting in inactivation of TNF-α" *J. Immunol.* 161:2636-2641 (1998).

Baliko, et al., "Th2 biased immune response in cases with active Mycobacterium tuberculosis infection and tuberculin anergy" *FEMS Immunol. Med. Micro.* 22:188-204 (1998).

Bermudez and Champsi, "Infection with Mycobacterium avium induces production of interleukin-10 (IL-10), and administration of anti-IL-10 antibody is associated with enhanced resistance to infection in mice" *Infect. Immun.* 61:3093-3097 (1993).

Beutler and Cerami, "The biology of cachectin/TNF-A primary mediator of the host response" *Ann. Rev. Immunol.* 7:625-655 (1989).

Blauer, et al., "Modulation of the antilisterial activity of human blood-derived macrophages by activating and deactivating cytokines" *J. Interferon Cytokine Res.* 15:105-114 (1995).

Boman, et al., "Phase I study of recombinant gamma-interferon (rIFN-γ)" *Journal of Biological Response Modifiers* 7:438-446 (1988).

Bruntsch, et al., "phase II study of recombinant human interferon-γ in metastatic renal cell carcinoma" *Journal of Biological Response Modifiers* 9:335-338 (1990).

Bukowski, et al., "Phase I trial of continuous infusion of recombinant interleukin-2 and intermittent recombinant interferon-$\alpha_{2a}$. Clinical effects" *Journal of Biological Response Modifiers* 9:538-545 (1990).

Caulfield, et al., "Phase I1-Ib trial of an anti-$G_{D3}$ monoclonal antibody in combination with interferon-α in patients with malignant melanoma" *Journal of Biological Response Modifiers* 9:319-328 (1990).

Chambrier, et al., "Hormonal and metabolic effects of chronic interleukin-2 infusion in cancer patients" *Journal of Biological Response Modifiers* 9:251-255 (1990).

Chouaib, et al., "More insights into the complex physiology of TNF" *Immunol. Today* 12(5):141-145 (1991).

Coclet-Ninin, et al., "Interferon-beta not only inhibits interleukin-1β and tumor necrosis factor-α but stimulates interleukin-1 receptor antagonist production in human peripheral blood mononuclear cells" *Eur. Cytokine Network* 8(4):345-349 (1997).

Colman, et al., *Hemostatsis and Thrombosis: Basic Principles and Clinical Practice 2nd. Edition* (Colman, et al., eds.) pp. 63-67 J.B. Lippincott: Philadelphia, PA 1987.

Cox, et al., "Phase II study of human lymphoblastoid interferon in patients with multiple myeloma" *Journal of Biological Response Modifiers* 7:318-325 (1988).

Creaven, et al., "Initial clinical trial of the macrophage activator muramyl tripeptide-phosphatidylethanolamine encapsulated in liposomes in patients with advanced cancer" *Journal of Biological Response Modifiers* 9:492-498 (1990).

Croghan, et al., "A phase I trial of recombinant interferon-α and α-difluoromethylornithine in metastatic melanoma" *Journal of Biological Response Modifiers* 7:409-415 (1988).

D'Andrea, et al., "Interleukin 10 (IL-10) inhibits human lymphocyte interferon γ production by suppressing natural killer cell stimulatory factor/IL-12 synthesis in accessory cells" *J. Exp. Med.* 178:1041-1048 (1993).

Dimery, et al., "Recombinant interferon-γ in the treatment of recurrent nasopharyngeal carcinoma" *Journal of Biological Response Modifiers* 8:221-226 (1989).

Dinarello, "Induction of interleukin-I and interleukin-I receptor antagonist" *Sem. In Oncol.* 24(No. 3, Suppl. 9):81-93 (1997).

Dupere, et al., "Patterns of cytokines released by peripheral blood leukocytes of normal donors and cancer patients during interleukin-2 activation in vitro" *Journal of Biological Response Modifiers* 9:140-148 (1990).

Englehardt, et al, "Biological response to intravenously administered endotoxin in patients with advanced cancer" *Journal of Biological Response Modifiers* 9:480-491 (1990).

Engelmann, et al., "Two tumor necrosis factor-binding proteins purified from human urine" *J. Biol. Chem.* 265(3):1531-1536 (1990).

Eriks and Emerson, "Temporal effect of tumor necrosis factor alpha on murine macrophages infected with Mycobacterium avium" *Infect. Immun.* 65(6):2100-2106 (1997).

Etges and Muller, "Progressive disease or protective immunity to Leishmania major infection: the result of a network of stimulatory and inhibitory interactions" *J. Mol. Med.* 76:372-390 (1998).

Fareed, et al., "Novel antigenic markers of human tumor regression" *Journal of Biological Response Modifiers* 7:11-23 (1988).

Favrot, et al., "Functional and immunophenotypic modifications induced by interleukin-2 did not predict response to therapy in patients with renal cell carcinoma" *Journal of Biological Response Modifiers* 9:167-177 (1990).

Fernandes and Baldwin, "Interleukin-10 downregulates protective immunity to Brucella abortus" *Infect. Immun.* 63:1130-1133 (1995).

Foon, et al., "A prospective randomized trial of $\alpha_{2B}$-interferon/γ-interferon or the combination in advanced metastatic renal cell carcinoma" *Journal of Biological Response Modifiers* 7:540-545 (1988).

Frost, et al., "Interleukin-6 induction by a muramyltripeptide derivative in cancer patients" *Journal of Biological Response Modifiers* 9:160-166 (1990).

Gadducci, et al., "Serum levels of soluble receptors for tumor necrosis factor (p55 and p75 sTNFr) in endometrial cancer" *Anticancer Res.* 16:3125-3128 (1996).

Gill, et al., "Interferon-alpha maintenance therapy after cytotoxic chemotherapy for treatment of acquired immunodeficiency syndrome-related kaposi's sarcoma" *Journal of Biological Response Modifiers* 9:512-516 (1990).

Greenblatt, et al., "The type B receptor for tumor necrosis factor-alpha" *Blood* 80:1339-1346 (1992).

Gustavson, et al., "Pharmacokinetics of teceleukin (Recombinant human interleukin-2) after intravenous or subcutaneous administration to patients with cancer" *Journal of Biological Response Modifiers* 8:440-449 (1989).

Handzel, et al., "Immunomodulation of T cell deficiency in humans by thymic humoral factor: from crude extract to synthetic thymic humoral factor-γ2" *Journal of Biological Response Modifiers* 9:269-278 (1990).

Hank, et al., "Depressed in vitro T cell responses concomitant with augmented interleukin-2 responses by lymphocytes from cancer patients following in vivo treatment with interleukin-2" *Journal of Biological Response Modifiers* 9:5-14 (1990).

Hercend, et al., "Immunotherapy with lymphokine-activated natural killer cells and recombinant interleukin-2: A feasibility trial in metastatic renal cell carcinoma" *Journal of Biological Response Modifiers* 9:546-555 (1990).

Herrmann, et al., "Stimulation of granulopoiesis in patients with malignancy by recombinant human granulocyte-macrophage colony-stimulating factor: Assessment of two routes of administration" *Journal of Biological Response Modifiers* 9:475-479 (1990).

Hertler, et al., "A phase I study of T101-ricin A chain immunotoxin in refractory chronic lymphocytic leukemia" *Journal of Biological Response Modifiers* 7:97-113 (1988).

Himmler, et al., "Molecular cloning and expression of human and rat tumor necrosis factor receptor chain (p60) and its soluble derivative, tumor necrosis factor-binding protein" *DNA and Cell Biol.* 9(10):705-715 (1990).

Jacobs, et al., "minimal antigenicity of intron A in human recipients demonstrated by three analytical methods" *Journal of Biological Response Modifiers* 7:447-456 (1988).

Jakobsen, et al., "Decreased antitoxic activities among children with clinical episodes of malaria" *Infect. Immun.* 66(4):1654-1659 (1998).

Jakschies, et al., "Emergence and decay of the human Ms homolog in cancer patients during and after interferon-α therapy" *Journal of Biological Response Modifiers* 9:305-312 (1990).

Kalmanti, et al., "Serum levels of tumor necrosis factor soluble interleukin 2 receptor as markers of disease activity and prognosis in childhood leukemia and lymphoma" *Int. J. Hematol.* 57:147-152 (1993).

Kaufmann, et al., "T cells and cytokines in intracellular bacterial infections: experiences with Mycobacterium bovis BCG" *Ciba Fdn. Symp.* 195:123-132 (1995).

Kellokumpu-Lehtinen, et al., "Recombinant interferon-α2a and vinblastine in advanced renal cell cancer: A clinical phase I-II study" *Journal of Biological Response Modifiers* 9:439-444 (1990).

Kessler, "Adsorptive plasma treatment: Optimization of extracorporeal devices and systems" *Blood Purification* 11:150-157 (1993).

Khazaeli, et al., "Initial evaluation of a human immunoglobulin M monoclonal antibody (HA-1A) in humans" *Journal of Biological Response Modifiers* 9:178-184 (1990).

Kolitz, et al., "Phase I trial of recombinant interleukin-2 and cyclophosphamide: Augmentation of cellular immunity and T-cell mitogenic response with long term administration of rIL-2" *Journal of Biological Response Modifiers* 7:457-472 (1988).

Krigel, et al., "Treatment of epidemic kaposi's sarcoma with a combination of interferon-alpha 2b and etoposide" *Journal of Biological Response Modifiers* 7:359-364 (1988).

Lantz, et al., "Infusion of tumor necrosis factor (TNF) causes an increase in circulating TNF-binding protein in humans" *Cytokine* 2(6):402-406 (1990).

Laszlo, et al., "Phase I studies of recombinant interferon-γ" *Journal of Biological Response Modifiers* 9:185-193 (1990).

Lentz, et al., "Apheresis of low molecular weight protein fraction and the onset of labor" *Journal of Clinical Apheresis* 5:62-67 (1990).

Lentz, "The phylogeny of oncology" *Mol. Biother.* 2:137-144 (1990).

Letterio and Roberts, "Regulation of immune responses by TGF-β" *Ann. Rev. Immuno.* 16:137-161 (1998).

Litton, et al., "Biological and clinical effects of the oral immunomodulator 3,6'Bis(2-piperidinoethoxy)acridine trihydrochloride in patients with malignancy" *Journal of Biological Response Modifiers* 9:61-70 (1990).

Lucey, et al., "Type 1 and type 2 cytokine dysregulation in human infectious, neoplastic, and inflammatory diseases" *Clin. Micro. Rev.* 9(4):532-562 (1996).

Maas, et al., "Interleukin-2 in cancer treatment: disappointing or (still) promising? A review" *Cancer Immunol. Immunother.* 36:141-148 (1993).

Maca, "Inhibition of the growth of lewis lung carcinoma by indomethacin in conventional, nude, and beige mice" *Journal of Biological Response Modifiers* 9:568-580 (1990).

Marshall, et al., "Effects of coumarin (12-benzopyrone) and cimetidine on peripheral blood lymphocytes, natural killer cells, and monocytes in patients with advanced malignancies" *Journal of Biological Modifiers* 8:62-69 (1989).

Marshall, et al., "Treatment of renal cell carcinoma with daily low-dose alpha-interferon" *Journal of Biological Response Modifiers* 8:453-461 (1989).

Miles, et al., "induction of soluble tumour necrosis factor receptors during treatment with interleukin-2" *Brit. J. Cancer* 66:1195-1199 (1992).

Mittelman, et al., "Treatment of patients with advanced cancer using multiple long-term cultured lymphokine-activated killer (LAK) cell infusions and recombinant human interleukin-2" *Journal of Biological Response Modifiers* 8:468-478 (1989).

Musiani, et al., "Effect of low doses of interleukin-2 injected perilymphatically and peritumorally in patients with advanced primary head and neck squamous cell carcinoma" *Journal of Biological Response Modifiers* 8:571-578 (1989).

Neidhart, "Phase I study of recombinant methionyl human consensus interferon (r-metHuIFN-Con)" *Journal of Biological Response Modifiers* 7:240-248 (1988).

Oratz, et al. "Induction of tumor-infiltrating lymphocytes in human malignant melanoma metastases by immunization to melanoma antigen vaccine" *Journal of Biological Response Modifiers* 8:355-358 (1989).

Oratz, et al., "Antimelanoma monoclonal antibody-ricin A chain immunoconjugate (XMMME-001-RTA) plus cyclophosphamide in the treatment of metastatic malignant melanoma: Results of a phase II trial" *Journal of Biological Response Modifiers* 9:345-354 (1990).

Pais, et al., "Pharmacokinetics of recombinant interleukin-2 in children with malignancies: A pediatric oncology group study" *Journal of Biological Response Modifiers* 9:517-521 (1990).

Paolozzi, et al., "Phase I trial of recombinant interleukin-2 and recombinant β-interferon in refractory neoplastic diseases" *Journal of Biological Response Modifiers* 8:122-139 (1989).

Perez, et al., "A phase I trial of recombinant human gamma interferon (IFN-$_{\gamma 4A}$) in patients with advanced malignancy" *Journal of Biological Response Modifiers* 7:309-317 (1988).

Quesada, et al., "Recombinant interferon alpha and gamma in combination as treatment for tetastatic renal cell carcinoma" *Journal of Biological Response Modifiers* 7:234-239 (1988).

Rabinowitz, et al., "Hemolytic anemia in a cancer patient treated with recombinant interferon-γ" *Journal of Biological Response Modifiers* 9:256-259 (1990).

Reimann, et al., "Suppression of the immune response by microorganisms" *Scand. J. Immunol.* 31:543-546 (1990).

Riffkin, et al., "Defense against the immune barrage: helminth survival strategies" *Immunol. Cell Bio* 74:564-574 (1996).

Romani, et al., "T helper cell dichotomy to *Candida albicans*: implications for pathology" *Immunol. Res.* 14:148-162 (1995).

Rosenthal, et al., "The in vitro function of lymphocytes from 25 cancer patients receiving four to seven consecutive days of recombinant IL-2" *Journal of Biological Response Modifiers* 7:123-139 (1988).

Rybak, et al., "Interferon therapy of relapsed and refractory hodgkin's disease: Cancer and leukemia group B study 8652" *Journal of Biological Response Modifiers* 9:1-4 (1990).

Sarna, et al., "Systemic administration of recombinant methionyl human interleukin-2 (Ala 125) to cancer patients: Clinical results" *Journal of Biological Response Modifiers* 8:16-24 (1989).

Sarna, et al., "A pilot study of intralymphatic interleukin-2. II. Clinical and biological effects" *Journal of Biological Response Modifiers* 9:81-86 (1990).

Sarthou, et al., "Prognostic value of anti-*Plasmodium falciparum*-specific immunoglobulin G3, cytokines, and their soluble receptors in west African patients with severe malaria" *Infect. Immun.* 65(8):3271-3276 (1997).

Sato, et al., "induction of bone formation in an adenoid cystic carcinoma of the maxillary sinus by adoptive immunotherapy involving intra-arterial injection of lympholine-activated killer cells and recombinant interleukin-2 in combination with radiotherapy" *Journal of Biological Response Modifiers* 9:329-334 (1990).

Schaadt, et al., "Phase II study of recombinant human tumor necrosis factor in colorectal carcinoma" *Journal of Biological Response Modifiers* 9:247-250 (1990).

Schall, et al., "molecular cloning and expression of a receptor for human tumor necrosis factor" *Cell* 61:361-370 (1990).

Scheithauer, et al., "Combined α-2C-interferon/VMCP polychemotherapy versus VMCP polychemotherapy a induction therapy in multiple myeloma: A prospective randomized trial" *Journal of Biological Response Modifiers* 8:109-115 (1989).

Schiller, et al., "A phase I trial of interferon-α-2a plus cyclophosphamide, vincristine, prednisone, and doxorubicin" *Journal of Biological Response Modifiers* 8:252-261 (1989).

Seckinger, et al., "Purification and biologic characterization of a specific tumor necrosis factor α inhibitor" *J. Biol. Chem.* 264(20):11966-11973 (1989).

Seigler, et al, "Melanoma patient antibody responses to melanoma tumor-associated antigens defined by murine monoclonal antibodies" *Journal of Biological Response Modifiers* 8:37-52 (1989).

Shau, et al., "A pilot study of intralymphatic interleukin-2. I. Cytotoxic and surface marker changes of peripheral blood lymphocytes" *Journal of Biological Response Modifiers* 9:71-80 (1990).

Sidhu and Bollon, "Tumor necrosis factor activities and cancer therapy—A perspective" *Pharmacol. Ther.* 57:79-128 (1993).

Sieling, et al., "Immunosuppressive roles for IL-10 and IL-4 in human infection" *J. Immunol.* 150(12):5501-5510 (1993).

Spriggs, "One step ahead of the game: Viral immunomodulatory molecules" *Ann. Rev. Immunol.* 14:101-130 (1996).

Steger, et al., "Long-term remission in a patient with erythroleukemia following interferon-α treatment" *Journal of Biological Response Modifiers* 8:351-354 (1989).

Steinmetz, et al., "Phase I study of 24-hour continuous intravenous infusion of recombinant human tumor necrosis factor" *Journal of Biological Response Modifiers* 7:417-423 (1988).

Sznol, et al., "A phase I study of high-dose interleukin-2 in combination with interferon $\alpha_{2b}$," *Journal of Biological Response Modifiers* 9:529-537 (1990).

Trigg, et al., "α-interferon therapy for lymphoproliferative disorders developing in two children following bone marrow transplants" *Journal of Biological Response Modifiers* 8:603-613 (1989).

Trinchieri, et al., "Cytokine cross-talk between phagocytic cells and lymphocytes: Relevance for differentiation/Activation of phagocytic cells and regulation of adaptive immunity" *J. Cell. Biochem.* 53:301-308 (1993).

Trump et al., "Interferon-α-n1 and continuous infusion vinblastine for treatment of advanced renal cell carcinoma" *Journal of Biological Response Modifiers* 9:108-111 (1990).

Umiel, et al., "Recombinant interleukin-2-activated intracavitary lymphocytes: Phenotypic characteristics and effector function" *Journal of Biological Response Modifiers* 8:409-421 (1989).

Von Hoff, et al., "Phase II evaluation of recombinant γ-interferon in patients with advanced pancreatic carcinoma: A southwest oncology group study" *Journal of Biological Response Modifiers* 9:584-587 (1990).

Walsh, et al., "Phase I study of the combination of alpha-2 interferon and cisplatinum" *Journal of Biological Response Modifiers* 8:11-15 (1989).

Weil-Hillman, et al., "Transient decrease in IL-2 responsive lymphocytes 24 hours after initiation of continuous IL-2 infusion in cancer patients" *Journal of Biological Response Modifiers* 7:424-437 (1988).

Whitehead, et al., "A phase II trial of recombinant tumor necrosis factor in patients with metastatic colorectal adenocarcinoma: A southwest oncology group study" *Journal of Biological Response Modifiers* 9:588-591 (1990).

Yelavarthi, et al., "Analysis of p60 and p80 tumor necrosis factor-alpha" *American Journal of Pathology* 143:1131-1141 (1993).

Zamkoff, et al., "A Phase I trial of subcutaneously administered recombinant tumor necrosis factor to patients with advanced malignancy" *Journal of Biological Response Modifiers* 8:539-552 (1989).

Dummer, "Circulating interleukin-2 receptors are a group of multimeric proteins with immunoreactivity for interleukin-2 receptor alpha, beta, and gamma chains", *J. Interferon Cytokine Res.*, 16(4):315-320 (1996).

K.A. Fitzgerald, et al, Cytokine Facts Book Second Edition, Academic Press New York, pp. 71 and 272 (2001).

Lotem, et al, "Hematopoietic cytokines inhibit apoptosis induced by transforming growth factor beta 1 and cancer chemotherapy compounds in myeloid leukemic cells", *Blood*, 80(7):1750-1757 (1992).

Novick, "Soluble cytokine receptors are present in normal human urine", *J. Exp. Med.*, 170(4):1409-1414 (1989).

Young, et al., "Increased recurrence and metastasis in patients whose primary head and neck squamous cell carcinomas secreted granulocyte-macrophage colony-stimulating factor and contained CD34+ natural suppressor cells", *International J. Cancer*, 74(1):69-74 (1997).

Rivas, et al., "Expression of granulocyte-macrophage colony-stimulating factor receptors in human prostate cancer", *Blood*, 91:1037-47 (1998).

U.S. Appl. No. 09/709,045, dated Nov. 10, 2000.

U.S. Appl. No. 09/699,003, dated Oct. 26, 2000

Agishi, Anion-blood contact (ABC reaction) in patients treated by LDL apheresis with dextran sulfate-cellulose column while receiving ACE inhibitors (letter). JAMA; 271:195-6(1994).

Banyai et al., "Therapeutic efficiency of lipoprotein(a) reduction by low-density lipoprotein immunoapheresis," *Metabolism* 47(9):1058-1064 (1998).

Cytologic, "Unleash Immunotherapy," CytoLogic non CDA info. doc , pp. 1-10 (Apr. 27, 2006).

Daugherty, et al., "Polymerase chain reaction facilitates the cloning, CDR-grafting, and rapid expression of a murine monoclonal antibody directed against the CD18 component of leukocyte integrins," *Nucl. Acids Res.* 19: 2471-2476 (1991).

Guyton and Hall, *Textbook of Medical Physiology* 9th ed. pp. 299.

Harlow et al., *Antibodies, A Laboratory Manual*, Chapter 13, "Immunoaffinity Purification," pp. 511-552, 1988.

*Hemostasis and Thrombosis: Basic Principles and Clinical Practice* 2nd Ed., Colman, R.W., et al., p. 263 (J.B.Lippincott, Philadelphia, PA 1987).

Hong et al., "Intercellular adhesion molecule-1 expression induced by interleukin (IL)-1 beta or an IL-1 beta fragment is blocked by an IL-1 receptor antagonist and a soluble IL-1 receptor," *Journal of Neuroimmunology*, 44(2):163-170 (1993).

IBM Technical Disclosure Bulletin, vol. 19, No. 3. Aug. 1976 pp. 765-768.

Jablonska & Peitruska, "Release of soluble tumor necrosis factor receptors from polymorphonuclear cells of breast cancer patients," *Arch ImmunofTher Exp (Warsz)*. 45(5-6):449-53 (1997).

Janeway, et al. *Immunobiology: The Immune System in Health and Disease*, 4th Ed. pp. 102.

Kaminska, et al. Clinical significance of serum cytokine measurements in untreated colorectal cancer patients: soluble tumor necrosis factor receptor type I—an independent prognostic factor, *Tumour Biol.* 26(4):186-94(2005).

Kaminska, et al "Pretreatment serum levels of cytokines and cytokine receptors in patients with non-small cell lung cancer, and correlations with clinicopathological features and prognosis. M-CSF - an independent prognostic factor," *Oncology* 70(2):115-25(2006).

Kojima, et al. "Effect of nafamostat mesilate on bradykinin generation during lowdensity lipoprotein apheresis using a dextran sulfate cellulose column," *ASAIO Trans* 37: 644-8(1991).

Maruyama, et al. "Evidence for aberrant activation of the interleukin-2 autocrine loop by HTLV-1-encoded p40x and T3/Ti complex triggering," *Cell.* 48(2):343-350(1987).

Mitteregger, et al., "In vitro cell culture systems as the basis for an extracorporeal blood purification strategy in multiorgan failure treatment", *Ther Apher.*, 3(3):257-63 (1999).

National Cancer Institute, "Biological Therapies for Cancer: Questions and Answers," National Cancer Institute FactSheet (Aug. 16, 2004).

Old, "Antitumor activity of microbial products and tumor necrosis factor, and Bonavida" B, et al., (eds): Tumor Necrosis Factor/Cachecin and Related Cytokines, Basell, Karger, p. 7 (1988).

Palaszynski,"Synthetic C-terminal peptide of IL-1 functions as a binding domain as well as an antagonist for the IL-1 receptor," *Biochemical and Biophysical Research Communications*, 147(1):204-211(1987).

Pennica et al., "Characterization of a recombinant extracellular domain of the type 1 tumor necrosis factor receptor: evidence for tumor necrosis factor-alpha induced receptor aggregationm," *Biochemistry* 31(4):1134-1141(1992).

Pennica et al.,"Biochemical characterization of the extracellular domain of the 75-kilodalton tumor necrosis factor receptor,"*Biochemistry* 32(12): 3131-3138(1993).

Product description: catalog No. AB-225-PB catalog of R&D Systems. (1994).

Product description: catalog No. AB-226-PB catalog of R&D Systems (1994).

Product description: catalog Nos. FAB225F catalog of R&D Systems (1998).

Product description: catalog Nos. MAB225 catalog of R&D Systems (1998).,.

Product description: catalog Nos. AF-425-Pb catalog of R&D Systems (1998).
Product description: of antibody AHR3912. Biosource catalog.
Shibata, et al., "Changes of cell-mediated immunity with an advance of cancer-relation to the th1/th2 balance and inhibitors of th1 cytokines", *Biotherapy*, 12(5):715-17 (1998).
Verma et al., "Antibody engineering: comparison of bacterial, yeast, insect and mammalian expression systems," *Journal of Immunological Methods*, 216(1-2):165-181(1998).
Warzocha, et al. "Tumor necrosis factor ligand-receptor system can predict treatment outcome in lymphoma patients," *J Clin Oncol.* 15(2):499-508(1997).
Winter, et al. "Synthetic human antibodies and a strategy for protein engineering," *FEBS Letters*, 430:92-94(1998).
Yamazaki et al. Biocompatibility of plasma separator of an improved cellulose acetate hollow fiber. In: Sieberth HG (ed). Plasma Exchange. New York: fk Schattauer, 45-51(1980).
Holohan, et al. "Regression of canine mammary carcinoma after immunoadsorption therapy,"*Cancer Res*. 42(9):3663-8(1982).
Lentz, et al. "Low Molecular weight Protein Apheresis and Regression of Breast Cancer", *Abstract in Japanese Society of Apheresis* 15 Supplement S31, W4-3(1996).
Suzuki, "A prospect of anti-cytokine therapy,", Igaku no Ayurni, Japan, lshiyaku Publishers, Inc., 167(5):432-435 (1993).
Olsson, "Isolation and characterization of a tumor necrosis factor binding protein from urine", *Eur. J. Haematol*., 42(3):270-275 (1989).
Peetre, "A tumor necrosis factor binding protein is present in human biological fluids", *Eur. J. Haematol*., 41(3):414-419 (1988).
Adolf and Frohbeis, "Monoclonal antibodies to soluble human TNF receptor (TNF binding protein) enhance its ability to block TNF toxicity.", *Cytokine*, 4(3):180-184 (1992).
Bjornberg, et al, "Mechanisms involved in the processing of the p. 55 and the p. 75 tumor necrosis factor (TNF) receptors to soluble receptor forms", Lymphokine Cytokine Res., 13(3):203-11 (1994).
Colman, et al., Hemostasis and Thrombosis: Basic Principles and Clinical Practice 2nd Ed., Colman, R.W., et al., p. 242-267 (J.B. Lippincott, Philadelphia, PA 1987).
Gadducci, et al., "Serum levels of tumor necrosis factor (TNF), soluble receptors for TNF (55- and 75-kDa sTNFr), and soluble CD14 (sCD14) in epithelial ovarian cancer", *Gynecol Oncol*, 58(2):184-8 (1995).
Grell, et al., "The type 1 receptor (CD120a) is the high-affinity receptor for soluble tumor necrosis factor", *Proc Nati Acad Sci U S A*., 95(2):570-5 (1998).
Grosen, et al, "Measurement of the soluble membrane receptors for tumor necrosis factor and lymphotoxin in the sera of patients with gynecologic malignancy", *Gynecol Oncol*, 50(1):68-77 (1993).
Hasegawa, et al., "Increased soluble tumor necrosis factor receptor levels in the serum of elderly people", *Gerontology*, 46(4):185-8 (2000).
Jablonska & Peitruska, "Release of soluble tumor necrosis factor receptors from polymorphonuclear cells of breast cancer patients," *Arch Immunol Ther Exp (Wersz)*. 45(5-6):449-53 (1997).
Jablonska, et al., "Tumor necrosis factor-alpha and soluble tumor necrosis factor receptors in the culture supernatants of polymorphonuclear cells and peripheral blood mononuclear cells from cancer patients", *Eur Cytokine Netw*, 9(2):155-9 (1998).
Laucella, et al., "Papel de las citoquinas en la resistencia y patologia durante la infeccion con *Trypanosome cruzi*" Revista Argentina de Microbiologia, 28:99-109 (1996) (with English Abstract).
Macallan, et al., "Development of a novel TNF alpha ligand-receptor binding assay for screening NATCHEM Libraries", *J Recept Signal Transduct Res*, 17(1-3):521-9 (1997). (with English Abstract).
Matschiner, et al., *Current Advances in Vitamin K Research*, pp. 135-140, (John W. Suttle, ed.) Elsevier Science Published Co., Inc., 1988.
Nophar, et al., "Soluble forms of tumor necrosis factor receptors (TNF-Rs). The cDNA for the type 1 TNF-R, cloned using amino acid sequence data of its soluble form, encodes both the cell surface and a soluble form of the receptor", *EMBO J*, 9(10):3269-78 (1990).

Onsrud, et al., "Comparison between soluble tumor necrosis factor receptors and CA125 in peritoneal fluids as a marker for epithelial ovarian cancer", *Gynecol Oncol*, 57(2)183-7 (1995).
Onsrud, et al., "Soluble tumor necrosis factor receptors and CA 125 in serum as markers for epithelial ovarian cancer", *Tumour Blot*, 17(2):90-6 (1996).
Tesarova, et al., "Soluble TNF and IL-2 receptors in patients with breast cancer", *Med Sci Monit*, 6(4):661-7 (2000).
Decision—Interlocutory Motion—Bd.R.123(b), Before the Board of Patent Appeals and Interferences, United States Patent and Trademark Office, Paper 125, May 22, 2007, at 2.
Decision on Motions, Before the Board of Patent Appeals and Interferences, United States Patent and Trademark Office, Paper 108, filed Jan. 25, 2007 (1-53).
Decision-Priority-Bd.R. 125(a), Before the Board of Patent Appeals and Interferences, United States Patent and Trademark Office, Paper 155, filed Jan. 9, 2008 (1-21).
Declaration under 37 C.F.R. 1.131 of Dr. Rigdon Lentz, filed Feb. 4, 2005.
Selinsky et al., "Multifaceted Inhibition of Anti-Tumor Immune Mechanisms by Soluble Tumor Necrosis Factor Receptor Type I," *Immunology* 94:88-93, 1998.
Transcript of Oral Hearing, Nov. 20, 2007, Paper 151, at 37, II, 4-8.
Transcript of Oral Hearing, Nov. 20, 2007, Paper 151, at 38, II. 11-13.
Transcript of Oral Hearing, Nov. 20, 2007, Paper 151, at 37, II. 4-8; at 38, II. 11-17.
"Howell Request for Rehearing (Of the Decision Denying Howell's Requests)" Before The Board Of Patent Appeals and Interferences, Interference No: 105,413, Feb. 8, 2008.
"Lentz Reply to Howell's Request for Rehearing" Before The Board Of Patent Appeals and Interferences, Interference No: 105,413, Mar. 7, 2008.
Complaint Under 35 U.S.C. § 146, *U.S. District Court, District of Columbia, Cytologic, Inc. and Colorado State Universtiy Research Foundation v. BioPheresis GmbH and BioPheresis Technologies, Inc*. 1:08-cv-00978-CKK, filed Jun. 6, 2008 (pp. 11).
Answer and Affirmative Defenses of Defendant BioPheresis Technologies, Inc. to Plaintiffs' Complaint Under 35 U.S.C. § 146, *U.S. District Court, District of Columbia, Cytologic, Inc. and Colorado State Universtiy Research Foundation v. BioPheresis GmbH and BioPheresis Technologies, Inc*. 1:08-cv-00978-Ckk, filed Sep. 4, 2008 (pp. 13).
Status Report Regarding Service of Process on Defendant BioPheresis GmbH, *U.S. District Court, District of Columbia, Cytologic, Inc. and Colorado State Universtiy Research Foundation v. BioPheresis GmbH and BioPheresis Technologies, Inc*. 1:08-cv-00978-Ckk, filed Oct. 24, 2008 (pp. 3).
Answer and Affirmative Defenses of Defendant BioPheresis Technologies, Inc. to Plaintiffs' Complaint Under 35 U.S.C. § 146, *U.S. District Court, District of Columbia, Cytologic, Inc. and Colorado State Universtiy Research Foundation v. BioPheresis GmbH and BioPheresis Technologies, Inc*. 1:08-cv-00978-CKK, filed Nov. 14, 2008 (pp. 12).
Motion for Summary Judgment to Vacate Interference Pursuant to 35 U.S.C. § 135(b)(1) and Request for Oral Hearing, *U.S. District Court, District of Columbia, Cytologic, Inc. and Colorado State Universtiy Research Foundation v. BioPheresis GmbH and BioPheresis Technologies, Inc*. 1:08-cv-00978-Ckk, filed Nov. 21, 2008 (pp. 223).
Defendants' Brief in Opposition to Plaintiffs' Motion for Summary Judgment, *U.S. District Court, District of Columbia, Cytologic, Inc. and Colorado State Universtiy Research Foundation v. BioPheresis GmbH and BioPheresis Technologies, Inc*. 1:08-cv-00978-Ckk, filed Dec. 12, 2008 (pp. 350).
Motion and Stipulation to Admit the Administrative Record of Interference 105, 413, *U.S. District Court, District of Columbia, Cytologic, Inc. and Colorado State Universtiy Research Foundation v. BioPheresis GmbH and BioPheresis Technologies, Inc*. 1:08-cv-00978-CKK, filed Dec. 22, 2008 (pp. 4).
Plaintiffs' Reply Brief in Support of Their Motion for Summary Judgment to Vacate Interference Pursuant to 35 U.S.C. § 135(b)(1), *U.S. District Court, District of Columbia, Cytologic, Inc. and Colo-* rado State Universtiy Research Foundation v. BioPheresis GmbH and BioPheresis Technologies, Inc. 1:08-cv-00978-CKK, filed Dec. 23, 2008 (pp. 9).
Notice of Filing, U.S. District Court, District of Columbia, Cytologic, Inc. and Colorado State Universtiy Research Foundation v. BioPheresis GmbH and BioPheresis Technologies, Inc. 1:08-cv-00978-CKK, filed Dec. 31, 2008 (pp. 2).
Notice of Filing, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 9, 2009 (pp. 211).
Notice of Filing, Large Additional Attachments, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 9, 2009 (pp. 300).
Notice of Withdrawal as Counsel of Record Admitted Pro Hac Vice, U.S. District Court, District of Columbia, Cytologic, Inc. and Colorado State Universtiy Research Foundation v. BioPheresis GmbH and BioPheresis Technologies, Inc. 1:08-cv-00978-CKK, filed Feb. 13, 2009 (pp. 2).
Notice of Argument Raised in Briefing, U.S. District Court, District of Columbia, Cytologic, Inc. and Colorado State Universtiy Research Foundation v. BioPheresis GmbH and BioPheresis Technologies, Inc. 1:08-cv-00978-CKK, filed Dec. 21, 2009 (pp. 2).
Defendants' Sur-Reply in Opposition to Plaintiffs' Motion for Summary Judgment, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 6, 2010 (pp. 9).
Plaintiffs' Motion for Leave to File a Sur-Surreply in Response to Defendants' Sur-Reply in Opposition to Plaintiffs' Motion for Summary Judgment, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 12, 2010 (pp. 27).
Plaintiffs' Sur-Surreply in Response to Defendants' Sur-Reply in Opposition to Plaintiffs' Motion for Summary Judgment, U.S. District Court, District of Columbia, Cytologic, Inc. and Colorado State Universtiy Research Foundation v. BioPheresis GmbH and BioPheresis Technologies, Inc. 1:08-cv-00978-CKK filed Jan. 15, 2010 (pp. 22).
Memorandum Opinion, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 15, 2010 (pp. 32).
Order, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 15, 2010 (pp. 1).
Order for Initial Scheduling Conference, U.S. District Court, District of Columbia, Cytologic, Inc. And Colorado State Universtiy Research Foundation v. BioPheresis Gmbh and BioPheresis Technologies, Inc. 1:08-cv-00978- Ckk, filed Jan. 19, 2010 (pp. 3).
Joint Emergency Motion to Continue Initial Scheduling Conference, U.S. District Court, District of Columbia, Cytologic, Inc. and Colorado State Universtiy Research Foundation v. BioPheresis GmbH and BioPheresis Technologies, Inc. 1:08-cv-00978-CKK, filed Jan. 29, 2010 (pp. 5).
Motion for Admission *Pro Hac Vice* of Alyson L. Wooten, U.S. District Court, District of Columbia, Cytologic, Inc. and Colorado State Universtiy Research Foundation v. BioPheresis GmbH and BioPheresis Technologies, Inc. 1:08-cv-00978-CKK, filed Feb. 4, 2010 (pp. 5).
Motion for Admission *Pro Hac Vice* of Susan A. Cahoon, U.S. District Court, District of Columbia, Cytologic, Inc. and Colorado State Universtiy Research Foundation v. BioPheresis GmbH and BioPheresis Technologies, Inc. 1:08-cv-00978-CKK, filed Feb. 12, 2010 (pp. 7).
Joint Statement Regarding Proposed Schedule, U.S. District Court, District of Columbia, Cytologic, Inc. and Colorado State Universtiy Research Foundation v. BioPheresis GmbH and BioPheresis Technologies, Inc. 1:08-cv-00978-CKK, filed Feb. 12, 2010 (pp. 6).
Notice of Certification, U.S. District Court, District of Columbia, Cytologic, Inc. and Colorado State Universtiy Research Foundation v. BioPheresis GmbH and BioPheresis Technologies, Inc. 1:08-cv-00978-CKK, filed Feb. 24, 2010 (pp. 3).
Howell Exhibit 2001, Filed on Oct. 2, 2007, "U.S. Appl. No. 09/709,045, Filed Nov. 10, 2000" Before The Board Of Patent Appeals and Interferences, Interference No: 105,413.
Howell Exhibit 2002, Filed on Oct. 2, 2007, "U.S. Appl. No. 60/164,695, Filed Nov. 10, 1999" Before The Board Of Patent Appeals and Interferences, Interference No: 105,413.
Howell Exhibit 2003, Filed on Oct. 2, 2007, "U.S. Appl. No. 09/699,003, Filed Oct. 26, 2000" Before the Board of Patent Appeals and Interferences, Interference No: 105,413.
Howell Exhibit 2004, Filed on Oct. 2, 2007, "U.S. Appl. No. 09/316,226, Filed May 21, 1999" Before The Board Of Patent Appeals and Interferences, Interference No: 105,413.
Howell Exhibit 2005 , Filed on Oct. 2, 2007, "Lentz U.S. Patent No. 6,231,536, Issued May 15, 2001" Before the Board of Patent Appeals and Interferences, Interference No: 105,413.
Howell Exhibit 2006, Filed on Oct. 2, 2007, "U.S. Appl. No. 09/083,307, Filed May 22, 1998" Before the Board of Patent Appeals and Interferences, Interference No: 105,413.
Howell Exhibit 2007, Filed on Oct. 2, 2007, "Lentz U.S. Patent No. 6,620,382, Issued Sep. 16, 2003" Before the Board of Patent Appeals and Interferences, Interference No: 105,413.
Howell Exhibit 2008, Filed on Oct. 2, 2007, "Howell et al. U.S. Patent No. 6,379,708, Issued Apr. 30, 2002" Before the Board of Patent Appeals and Interferences, Interference No: 105,413.
Howell Exhibit 2009, Filed on Oct. 2, 2007, "Response Dated Jan. 22, 2003 in U.S. Appl. No. 09/709,045" Before The Board Of Patent Appeals and Interferences, Interference No: 105,413.
Howell Exhibit 2010 , Filed on Oct. 2, 2007, "Response Dated May 6, 2005 in U.S. Appl. No. 09/709,045" Before The Board Of Patent Appeals and Interferences, Interference No: 105,413.
Howell Exhibit 2011 "Lentz 37 C..F.R 41.202 Suggestion Of An Interference, Submitted May 6, 2005" Before The Board Of Patent Appeals and Interferences, Interference No: 105,413.
Howell Exhibit 2012, Filed on Oct. 2, 2007, "Declaration Of Donald Hillebrand, M.D. With Curriculum Vitae" Before The Board Of Patent Appeals and Interferences, Interference No: 105,413.
Howell Exhibit 2013, Filed on Oct. 2, 2007, "Office Action Dated Oct. 24, 2002 in U.S. Appl. No. 09/699,003" Before The Board Of Patent Appeals and Interferences, Interference No: 105,413.
Howell Exhibit 2014 , Filed on Oct. 2, 2007, "Office Action Dated Jul. 29, 2003 in U.S. Appl. No. 09/709,045" Before The Board Of Patent Appeals and Interferences, Interference No: 105,413.
Howell Exhibit 2015, Filed on Oct. 2, 2007, "Selinsky et al., "Multifaceted Inhibition Of Anti-Tumour Immune Mechanisms Bysoluble Tumour Necrosis Factor Receptor Type I," 94 Immunology 88-93 (1998)" Before The Board Of Patent Appeals and Interferences, Interference No: 105,413.
Howell Exhibit 2016 , Filed on Oct. 2, 2007, "Van Zee et al., "Tumor Necrosis Factor Soluble Receptors Circulate During Experimental And Clinical Inflammation And Can Protect, Against Excessive Tumor Necrosis Factor A In Vitro and In Vivo, 89 Proc. Natl. Acad. Sci. 4845-49 (Jun. 1992) Before The Board Of Patent Appeals and Interferences, Interference No: 105,413.
Howell Exhibit 2017 , Filed on Oct. 2, 2007, "Lentz U.S. Patent No. 4,708,713, Issued Nov. 24, 1987" Before The Board Of Patent Appeals and Interferences, Interference No: 105,413.
Howell Exhibit 2018, Filed on Oct. 2, 2007, "Maraskovsky et al. U.S. Patent No. 6,017,527, Issued Jan. 25, 2000" Before The Board Of Patent Appeals and Interferences, Interference No: 105,413.
Howell Exhibit 2019 , Filed on Oct. 2, 2007, "Response Dated Oct. 29, 2003 in U.S. Appl. No. 09/709,045" Before The Board Of Patent Appeals and Interferences, Interference No: 105,413.
Howell Exhibit 2020, Filed on Oct. 2, 2007, "Office Action Dated Feb. 25, 2004 in U.S. Appl. No. 09/709,045" Before The Board Of Patent Appeals and Interferences, Interference No: 105,413.
Howell Exhibit 2021, Filed on Oct. 2, 2007, "Response Dated Apr. 16, 2004 in U.S. Appl. No. 09/709,045" Before The Board Of Patent Appeals and Interferences, Interference No: 105,413.

Howell Exhibit 2022, Filed on Oct. 2, 2007, "Office Action Dated Jul. 12, 2004 in U.S. Appl. No. 09/709,045" Before The Board Of Patent Appeals and Interferences, Interference No: 105,413.

Howell Exhibit 2023, Filed on Oct. 2, 2007, "Böet al. U.S. Patent No. 5,817,528, Issued Oct. 6, 1998" Before The Board Of Patent Appeals and Interferences, Interference No: 105,413.

Howell Exhibit 2024, Filed on Oct. 2, 2007, "Schneider U.S. Patent No. 4,512,763, Issued Apr. 23, 1985" Before The Board Of Patent Appeals and Interferences, Interference No: 105,413.

Howell Exhibit 2025, Filed on Oct. 2, 2007, "Hoogenboom et al. U.S. Patent No. 5,565,332, Issued Oct. 15, 1996" Before The Board Of Patent Appeals and Interferences, Interference No: 105,413.

Howell Exhibit 2026, Filed on Oct. 2, 2007, "Response Filed Oct. 6, 2004 in U.S. Appl. No. 09/709,045" Before The Board Of Patent Appeals and Interferences, Interference No: 105,413.

Howell Exhibit 2027, Filed on Oct. 2, 2007, "Claim Summary Of U.S. Appl. No. 09/083,307" Before The Board Of Patent Appeals and Interferences, Interference No: 105,413.

Howell Exhibit 2028, Filed on Oct. 2, 2007, "Claim Summary of U.S. Appl. No. 09/316,226" Before The Board Of Patent Appeals and Interferences, Interference No: 105,413.

Howell Exhibit 2029, Filed on Oct. 2, 2007, "Claim Summary Of U.S. Appl. No. 09/699,003" Before The Board Of Patent Appeals and Interferences, Interference No: 105,413.

Howell Exhibit 2030, Filed on Oct. 2, 2007, "Claim Summary of U.S. Appl. No. 09/709,045" Before The Board Of Patent Appeals and Interferences, Interference No: 105,413.

Howell Exhibit 2031, Filed on Oct. 2, 2007, "Response Filed Nov. 1, 2000 In U.S. Appl. No. 09/444,144" Before The Board Of Patent Appeals and Interferences, Interference No: 105,413.

Howell Exhibit 2032, Filed on Oct. 2, 2007, "Office Action Dated Aug. 18, 2000 In U.S. Application Serial No. 09/444,144" Before The Board Of Patent Appeals and Interferences, Interference No: 105,413.

Howell Exhibit 2033 "Response Filed Feb. 20, 2001 in U.S. Appl. No. 09/444,144" Before The Board Of Patent Appeals and Interferences, Interference No: 105,413.

Howell Exhibit 2034, Filed on Oct. 2, 2007, "Howell 37 C.F.R. 1.132 Declaration Filed In U.S. Appl. No. 09/444,144" Before The Board Of Patent Appeals and Interferences, Interference No: 105,413.

Howell Exhibit 2035, Filed on Oct. 2, 2007, "Response Filed Oct. 23, 2001 Filed in U.S. Appl. No. 09/444,144" Before The Board Of Patent Appeals and Interferences, Interference No: 105,413.

Howell Exhibit 2036, Filed on Oct. 2, 2007, "Office Action Dated Aug. 10, 2001 in U.S. Appl. No. 09/444,144" Before The Board Of Patent Appeals and Interferences, Interference No: 105,413.

Howell Exhibit 2037, Filed on Oct. 2, 2007, "Japanese Publication No. 02045064 published Feb. 15,1990" *Before The Board Of* Patent Appeals and Interferences, Interference No: 105,413.

Howell Exhibit 2038, Filed on Oct. 2, 2007, "Response Filed On Dec. 1, 2003 in U.S. Appl. No. 09/699,003" Before The Board Of Patent Appeals and Interferences, Interference No: 105,413.

Howell Exhibit 2039, Filed on Oct. 2, 2007, "Certified English Translation of Japanese Publication No. 02045064" Before The Board Of Patent Appeals and Interferences, Interference No: 105,413.

Howell Exhibit 2040, Filed on Oct. 2, 2007, "Lentz's Alleged Support For Lentz Claims 23-41" Before The Board Of Patent Appeals and Interferences, Interference No: 105,413.

Howell Exhibit 2041, Filed on Oct. 2, 2007, "Decision In *University Of Iowa Research Found*. V. *Regents Of The Univ. Of California*, Interference No. 105,171, Paper No. 129 (Mar. 10, 2005)" Before The Board Of Patent Appeals and Interferences, Interference No: 105,413.

Howell Exhibit 2042, Filed on Oct. 2, 2007, "Comparison Chart for Alleged Support/Crtp" Before The Board Of Patent Appeals and Interferences, Interference No: 105,413.

Howell Exhibit 2043, Filed on Oct. 2, 2007, "Second Declaration Of Donald Hillebrand, M.D." Before The Board Of Patent Appeals and Interferences, Interference No: 105,413.

Howell Exhibit 2044, Filed on Oct. 2, 2007, "E-Mail From Chico Gholz on Feb. 23, 2006" Before The Board Of Patent Appeals and Interferences, Interference No: 105,413.

Howell Exhibit 2045, Filed on Oct. 2, 2007, "Warning Letter to Meredith Rigdon Lentz, M.D. From Food and Drug Administration On Aug. 21, 2001" Before The Board Of Patent Appeals and Interferences, Interference No: 105,413.

Howell Exhibit 2046, Filed on Oct. 2, 2007, "Transcript Of Donald Hillebrand's Deposition on Jun. 20, 2006 With Errata Sheet" Before The Board Of Patent Appeals and Interferences, Interference No: 105,413.

Howell Exhibit 2047, Filed on Oct. 2, 2007, "Third Declaration Of Donald Hillebrand, M.D." Before The Board Of Patent Appeals and Interferences, Interference No: 105,413.

Howell Exhibit 2048, Filed on Oct. 2, 2007, "Rule 131 Declaration Filed in U.S. Appl. No. 09/444,144" Before The Board Of Patent Appeals and Interferences, Interference No: 105,413.

Howell Exhibit 2049, Filed on Oct. 2, 2007, "Attachments To Rule 131 Declaration Filed in U.S. Appl. No. 09/444,144" Before The Board Of Patent Appeals and Interferences, Interference No: 105,413.

Howell Exhibit 2050, Filed on Oct. 2, 2007, "Declaration Pursuant to 37 C.F.R.§ 1.31" Before The Board Of Patent Appeals And Interferences, Interference No: 105,413.

Howell Exhibit 2051, Filed on Oct. 2, 2007, "Selinsky Dissertation" Before The Board Of Patent Appeals and Interferences, Interference No: 105,413.

Howell Exhibit 2052, Filed on Oct. 2, 2007, "Mar. - Nov. 1999 Diligence Documents" Before The Board Of Patent Appeals and Interferences, Interference No: 105,413.

Howell Exhibit 2053, Filed on Oct. 2, 2007, "Lentz, M. R., "Continuous Whole Blood Ultrapheresis Procedure In Patients With Metastatic Cancer", Journal Of Biological Response Modifiers, vol. 8, pp. 511-527 (1989)" Before The Board Of Patent Appeals and Interferences, Interference No: 105,413.

Howell Exhibit 2054, Filed on Oct. 2, 2007, "Lentz, R., et al., "Low Molecular Weight Protein Apheresis And Regression Of Breast Cancer, Japanese Journal Of Apheresis, vol. 15, pp. 107-114 (1997) Before The Board Of Patent Appeals and Interferences, Interference No: 105,413.

Howell Exhibit 2055, Filed on Oct. 2, 2007, "E-Mail Regarding Publication Date Of Lentz 1997 Paper (Exhibit 2054)" Before The Board Of Patent Appeals and Interferences, Interference No: 105,413.

Howell Exhibit 2056, Filed on Oct. 2, 2007, "Boroughs And Selinsky Notebook Pages" Before The Board Of Patent Appeals and Interferences, Interference No: 105,413.

Howell Exhibit 2057, Filed on Oct. 2, 2007, "Howell/Lentz Family Tree" Before The Board Of Patent Appeals and Interferences, Interference No: 105,413.

Howell Exhibit 2058, Filed on Oct. 2, 2007, "Howell Research Proposal" Before The Board Of Patent Appeals and Interferences, Interference No: 105,413.

Howell Exhibit 2059, Filed on Oct. 2, 2007, "Chart In Support Of New 131 Declaration (Exhibit 2050)" Before The Board Of Patent Appeals and Interferences, Interference No: 105,413.

Howell Exhibit 2060, Filed on Oct. 2, 2007, "Textbook Of Medical Physiology, 9th Ed., Arthur C. Guyton, M.D. And John E. Hall, Ph.D, p. 299" Before The Board Of Patent Appeals and Interferences, Interference No: 105,413.

Howell Exhibit 2061, Filed on Oct. 2, 2007, "Immuno Biology, 4th Ed., p. 102" Before The Board Of Patent Appeals and Interferences, Interference No: 105,413.

Howell Exhibit 2062, Filed on Oct. 2, 2007, "Regents Of *The Univ. Of California* v. *Univ. Of Iowa Research Found*., No. 05-1374, (Fed. Cir. Jul. 17, 2006)" Before The Board Of Patent Appeals and Interferences, Interference No: 105,413.

Howell Exhibit 2063, Filed on Oct. 2, 2007, "Declaration Of Mark D. Howell, Cheryl I. Selinsky And Leland C. Leber, With Attachments, Filed in U.S. Appl. No. 09/444,144 On Oct. 23, 2001" Before The Board Of Patent Appeals and Interferences, Interference No: 105,413.

Howell Exhibit 2064, Filed on Oct. 2, 2007, "Declaration Of Mark D. Howell, Ph.D." Before The Board Of Patent Appeals and Interferences, Interference No: 105,413.

Howell Exhibit 2065, Filed on Oct. 2, 2007, "Transcript Of Donald Hillebrand's Deposition On Aug. 9, 2006" Before The Board Of Patent Appeals and Interferences, Interference No: 105,413.
Howell Exhibit 2066, Filed on Oct. 2, 2007, "Fourth Declaration of Donald J. Hillebrand, M.D" Before The Board Of Patent Appeals and Interferences, Interference No: 105,413.
Howell Exhibit 2067, Filed on Oct. 2, 2007, "Bernstein et al., U.S. Patent No. 4,863,611; Issued Sep. 5, 1989" Before The Board Of Patent Appeals and Interferences, Interference No: 105,413.
Howell Exhibit 2070, Filed on Oct. 2, 2007, "Fifth Declaration of Donald J. Hillebrand, M.D." Before The Board Of Patent Appeals and Interferences, Interference No: 105,413.
Howell Exhibit 2071, Filed on Oct. 2, 2007, "Curriculum vitae of Don Gray" Before The Board Of Patent Appeals and Interferences, Interference No: 105,413.
Howell Exhibit 2072, Filed on Oct. 2, 2007, "Attachment to Howell Priority Statement" Before The Board Of Patent Appeals and Interferences, Interference No: 105,413.
Howell Exhibit 2073, Filed on Oct. 2, 2007, "Sixth Declaration of Donald J. Hillebrand, M.D." Before The Board Of Patent Appeals and Interferences, Interference No: 105,413.
Howell Exhibit 2074, Filed on Oct. 2, 2007, "1994 Howell Research Proposal" Before The Board Of Patent Appeals and Interferences, Interference No: 105,413.
Howell Exhibit 2075, Filed on Oct. 2, 2007, "Selinsky and Howell (2000) (Soluble Tumor Necrosis Factor Receptor Type I Enhances Tumor Development and Persistence in Vivo), Cellular Immunology 200:81-87" Before The Board Of Patent Appeals and Interferences, Interference No: 105,413.
Howell Exhibit 2076, Filed on Oct. 2, 2007, "Declaration of Don Gray" Before The Board Of Patent Appeals and Interferences, Interference No: 105,413.
Howell Exhibit 2077, Filed on Oct. 2, 2007, "Declaration of Theresa A. Brown, Esq." Before The Board Of Patent Appeals and Interferences, Interference No: 105,413.
Howell Exhibit 2078, Filed on Oct. 2, 2007, "Second Declaration of Mark D. Howell, Ph.D." Before The Board Of Patent Appeals and Interferences, Interference No: 105,413.
Howell Exhibit 2079, Filed on Oct. 2, 2007, "Declaration of Cheryl L. Selinsky, Ph.D." Before The Board Of Patent Appeals and Interferences, Interference No: 105,413.
Howell Exhibit 2080, Filed on Oct. 2, 2007, "Declaration of Karen L. Boroughs" Before The Board Of Patent Appeals and Interferences, Interference No: 105,413.
Howell Exhibit 2081, Filed on Oct. 2, 2007, "Declaration of Dennis Murphy" Before The Board Of Patent Appeals and Interferences, Interference No: 105,413.
Howell Exhibit 2082, Filed on Oct. 2, 2007, "Declaration of Ned Daugherty" Before The Board Of Patent Appeals and Interferences, Interference No: 105,413.
Howell Exhibit 2083, Filed on Oct. 2, 2007, "Declaration of Wayne Halsey" Before The Board Of Patent Appeals and Interferences, Interference No: 105,413.
Howell Exhibit 2084, Filed on Oct. 2, 2007, "Comparison Table Providing Exemplary Evidence of Howell's Conception" Before The Board Of Patent Appeals and Interferences, Interference No: 105,413.
Howell Exhibit 2085, Filed on Oct. 2, 2007, Original draft of Howell U.S. Appl. No. 09/444,144, filed Nov. 6 20, 1999 ("The '144 application") Before The Board Of Patent Appeals and Interferences, Interference No: 105,413.
Howell Exhibit 2086, Filed on Oct. 2, 2007," New Client/File Maintenance Sheet for the '144 application file" Before The Board Of Patent Appeals and Interferences, Interference No: 105,413.
Howell Exhibit 2087, Filed on Oct. 2, 2007, "Lab Notebook of Cheryl Selinsky - STNFR Project Book 3 (Oct. 8, 1996-Jan. 26, 1998)" Before The Board Of Patent Appeals and Interferences, Interference No: 105,413.
Howell Exhibit 2088, Filed on Oct. 2, 2007, "Lab Notebook of Cheryl Selinsky - STNFR Project Book 4 (Jan. 20, 1998-Sep. 13, 1998)" Before The Board Of Patent Appeals and Interferences, Interference No: 105,413.
Howell Exhibit 2089, Filed on Oct. 2, 2007, "Lab Notebook of Cheryl Selinsky - STNFR Project Book 5 (Jan. 1999-Mar. 2000)" Before The Board Of Patent Appeals and Interferences, Interference No: 105,413.
Howell Exhibit 2090, Filed on Oct. 2, 2007, "Lab Notebook of Wayne A. Halsey Jr. - STNFR Project" Before The Board Of Patent Appeals and Interferences, Interference No: 105,413.
Howell Exhibit 2091, Filed on Oct. 2, 2007, "Excerpts from Lab Notebook of Karen L. Boroughs - STNFR Project Book 4" Before The Board Of Patent Appeals and Interferences, Interference No: 105,413.
Howell Exhibit 2092, Filed on Oct. 2, 2007, "Excerpts from Lab Notebook of Karen L. Boroughs - STNFR Project Book 5" Before The Board Of Patent Appeals and Interferences, Interference No: 105,413.
Howell Exhibit 2093, Filed on Oct. 2, 2007, "Excerpts from Lab Notebook of Karen L. Boroughs - STNFR Project Book 6" Before The Board Of Patent Appeals and Interferences, Interference No: 105,413.
Howell Exhibit 2094, Filed on Oct. 2, 2007, "Second Draft of the '144 Application" Before The Board Of Patent Appeals and Interferences, Interference No: 105,413.
Howell Exhibit 2095, Filed on Oct. 2, 2007, "Third Draft of the '144 Application" Before The Board Of Patent Appeals and Interferences, Interference No: 105,413.
Howell Exhibit 2096, Filed on Oct. 2, 2007, "Fourth Draft of the '144 Application" Before The Board Of Patent Appeals and Interferences, Interference No: 105,413.
Howell Exhibit 2097, Filed on Oct. 2, 2007, "Diligence Chart" Before The Board Of Patent Appeals and Interferences, Interference No: 105,413.
Howell Exhibit 2098, Filed on Oct. 2, 2007, "Response to Office Action Dated Feb. 4, 2005 in U.S. Appl. No. 09/699,003" Before The Board Of Patent Appeals and Interferences, Interference No: 105,413.
Howell Exhibit 2099, Filed on Oct. 2, 2007, "Dated version of Exhibit 2056" Before The Board Of Patent Appeals and Interferences, Interference No: 105,413.
Howell Exhibit 2100, Filed on Oct. 2, 2007, "Transcript of Leland Leber's deposition on Apr. 4, 2007" Before The Board Of Patent Appeals and Interferences, Interference No: 105,413.
Howell Exhibit 2101, Filed on Oct. 2, 2007, "Third Declaration of Mark D. Howell, Ph.D." Before The Board Of Patent Appeals and Interferences, Interference No: 105,413.
Howell Exhibit 2102, Filed on Oct. 2, 2007, "Declaration of Erin M. Dunston" Before The Board Of Patent Appeals and Interferences, Interference No: 105,413.
Howell Exhibit 2103, Filed on Oct. 2, 2007, "Gatanaga et al., (Purification and characterization of an inhibitor (soluble tumor necrosis factor receptor) for tumor necrosis factor and lymphotoxin obtained from the serum ultrafiltrates of human cancer patients", Proc. Natl. Acad. Sci (1990) 87:8781-8784 Before The Board Of Patent Appeals and Interferences, Interference No: 105,413.
Howell Exhibit 2104, Filed on Oct. 2, 2007, "Brockhaus et al., U.S. Patent No. 5,610,279 issued Mar. 11, 1997" Before The Board Of Patent Appeals and Interferences, Interference No: 105,413.
Howell Exhibit 2105, Filed on Oct. 2, 2007, "Brockhaus et al., U.S. Patent No. 5,808,029 issued Sep. 15, 1998" Before The Board Of Patent Appeals and Interferences, Interference No: 105,413.
Lentz Exhibit 1001, Filed Oct. 20, 2006, "First Declaration Of Peter Sims" Before The Board Of Patent Appeals and Interferences, Interference No: 105,413.
Lentz Exhibit 1002, Filed Oct. 20, 2006, "Cv Of Peter Sims" Before The Board Of Patent Appeals and Interferences, Interference No: 105,413.
Lentz Exhibit 1003, Filed on Oct. 20, 2006, "*Decision In University Of Iowa Research Foundation* v. *The Regents Of The University Of California*, Interference No. 105,171, Paper No. 129, Mar. 10, 2005" Before The Board Of Patent Appeals and Interferences, Interference No: 105,413.
Lentz Exhibit 1004, Filed Oct. 20, 2006, "Office Action Dated Jan. 6, 2005 in U.S. Appl. No. 09/709,045" Before The Board Of Patent Appeals and Interferences, Interference No: 105,413.

Lentz Exhibit 1005, Filed Oct. 20, 2006, "Copy Of Date Stamped Page From the Journal Issued Containing The Selinsky et al. 1998 Reference Obtained From The British Library" Before The Board Of Patent Appeals and Interferences, Interference No: 105,413.

Lentz Exhibit 1006, Filed Oct. 20, 2006, "Memorandum Entitled (Review Of Ultrapheresis System Of Dr. Rigdon Lentz) Prepared by Dr. George C. Fareed And Dated Sep. 4, 1990" Before The Board Of Patent Appeals and Interferences, Interference No: 105,413.

Lentz Exhibit 1008, Filed Oct. 20, 2006, "U.S. Appl. No. 09/709,045" Before The Board Of Patent Appeals and Interferences, Interference No: 105,413.

Lentz Exhibit 1009, Filed Oct. 20, 2006, "Second Declaration Of Peter Sims" Before The Board Of Patent Appeals and Interferences, Interference No: 105,413.

Lentz Exhibit 1010, Filed Oct. 20, 2006, "U.S. Appl. No. 60/164,695" Before The Board Of Patent Appeals and Interferences, Interference No: 105,413.

Lentz Exhibit 1011, Filed Oct. 20, 2006, "Provisional Application Filing Sheet for U.S. Appl. No. 60/164,695" Before The Board Of Patent Appeals and Interferences, Interference No: 105,413.

Lentz Exhibit 1012, Filed Oct. 20, 2006, "Application Filing Sheet For U.S. Appl. No. 09/709,045" Before The Board Of Patent Appeals and Interferences, Interference No: 105,413.

Lentz Exhibit 1013, Filed Oct. 20, 2006, "U.S. Patent No. 4,512,763" Before The Board Of Patent Appeals and Interferences, Interference No: 105,413.

Lentz Exhibit 1014, Filed Oct. 20, 2006, "Lentz, "The Role Of Therapeutic Apheresis in The Treatment of Cancer: A Review," Thereapeutic Apheresis, 3(1) 1999, pp. 40-49" Before The Board Of Patent Appeals and Interferences, Interference No: 105,413.

Lentz Exhibit 1015, Filed Oct. 20, 2006, "U.S. Copyright Office Search Records Results For Lentz, "The Role of Therapeutic Apheresis In The Treatment Of Cancer: A Review," Therapeutic Apheresis, 3(1) 1999, pp. 40-49" Before The Board Of Patent Appeals and Interferences, Interference No: 105,413.

Lentz Exhibit 1016, Filed Oct. 20, 2006, "Description Of The Product Identified As Catalog No. Ab-225-Pb In The 1994 Catalog Of R&D Systems" Before The Board Of Patent Appeals and Interferences, Interference No: 105,413.

Lentz Exhibit 1017, Filed Oct. 20, 2006, "The Description Of The Product Identified As Catalog No. Ab-226-Pb In The 1994 Catalog Of R&D Systems" Before The Board Of Patent Appeals and Interferences, Interference No: 105,413.

Lentz Exhibit 1018, Filed Oct. 20, 2006, "The Description of Catalog Nos. Fab225f, Mab225, And Af-425-Pb In The 1998 Catalog Of R&D Systems" Before The Board Of Patent Appeals and Interferences, Interference No: 105,413.

Lentz Exhibit 1019, Filed Oct. 20, 2006, "U.S. Patent No. 4,439,322" Before The Board Of Patent Appeals and Interferences, Interference No: 105,413.

Lentz Exhibit 1020, Filed Oct. 20, 2006, "Verma et al., Journal of Immunological Methods, 216 (1988), 165-181" Before The Board Of Patent Appeals and Interferences, Interference No: 105,413.

Lentz Exhibit 1021, Filed Oct. 20, 2006, "Winter, Febs Letters, 430 (1998), 92-94" Before The Board Of Patent Appeals and Interferences, Interference No: 105,413.

Lentz Exhibit 1022, Filed Oct. 20, 2006, "Yamazaki Z, Inoue N, Fujimori Y, et al. Biocompatibility Of Plasma Seperator Of An Improved Cellulose Acetate Hollow Fiber. In: Sieberth Hg (Ed). Plasma Exchange. New York: Fk Schattauer, 1980: 45-51" Before The Board Of Patent Appeals and Interferences, Interference No: 105,413.

Lentz Exhibit 1023, Filed Oct. 20, 2006, "Kojima S, Harada-Shiba M, Nomura S, et al. Effect of Nafamostat Mesilate on Bradykinin Generation During Lowdensity Lipoprotein Apheresis Using a Dextran Sulfate Cellulose Column. Asaio Trans 1991; 37. 644-8" Before The Board Of Patent Appeals and Interferences, Interference No: 105,413.

Lentz Exhibit 1024, Filed Oct. 20, 2006, "Agishi T. Anion-Blood Contact (Abc Reaction) In Patients Treated by Ldl Apheresis With Dextran Sulfate-Cellulose Column While Receiving Ace Inhibitors (Letter). Jama 1994; 271: 195-6" Before The Board Of Patent Appeals and Interferences, Interference No: 105,413.

Lentz Exhibit 1025, Filed Oct. 20, 2006, "U.S. 4,191,182" Before The Board Of Patent Appeals and Interferences, Interference No: 105,413.

Lentz Exhibit 1026, Filed Oct. 20, 2006, "Information Regarding R&D Systems Printed From Http://www.Rndsystems.Com/Home.Aspx, Http://www.Rndsystems.Com/Customer_Service.Aspx, and Http://www.Rndsystems.Com/About_Us.Aspx" Before The Board Of Patent Appeals and Interferences, Interference No: 105,413.

Lentz Exhibit 1027, Filed Oct. 20, 2006, "Page 1 Of An Email Dated Apr. 13, 2006 From Mr. Paul Nealy Of R&D Systems To Dr. James J. Kelly" Before The Board Of Patent Appeals and Interferences, Interference No: 105,413.

Lentz Exhibit 1028, Filed Oct. 20, 2006, "Hong et al., Journal Of Neuroimmunology, 44 (1993) 163-170" Before The Board Of Patent Appeals and Interferences, Interference No: 105,413.

Lentz Exhibit 1029, Filed Oct. 20, 2006, "Palaszynski, Biochemical And Biophysical Research Communications, 147,1987, 204-211" Before The Board Of Patent Appeals and Interferences, Interference No: 105,413.

Lentz Exhibit 1030, Filed Oct. 20, 2006, "U.S. Patent No. 6,133,431" Before The Board Of Patent Appeals and Interferences, Interference No: 105,413.

Lentz Exhibit 1031, Filed Oct. 20, 2006, "Date-Stamped Cover Of The Journal Containing Verma et al. Obtained From The British Library" Before The Board Of Patent Appeals and Interferences, Interference No: 105,413.

Lentz Exhibit 1032, Filed Oct. 20, 2006, "Date-Stamped Cover Of The Journal Containing Winter Obtained From the British Library" Before The Board Of Patent Appeals and Interferences, Interference No: 105,413.

Lentz Exhibit 1034, Filed Oct. 20, 2006, "Banyai et al., Metabolism, vol. 47, No. 9 (Sep.), 1998, pp. 1058-1064" Before The Board Of Patent Appeals and Interferences, Interference No: 105,413.

Lentz Exhibit 1035, Filed Oct. 20, 2006, "U.S. Copyright Office Search Records Results for Banyai et al., Metabolism, vol. 47, No. 9 (Sep.), 1998, pp. 1058-1064" Before The Board Of Patent Appeals and Interferences, Interference No: 105,413.

Lentz Exhibit 1036, Filed Oct. 20, 2006, "A Description of Antibody Ahr3912 From The Biosource Catalog" Before The Board Of Patent Appeals and Interferences, Interference No: 105,413.

Lentz Exhibit 1037, Filed Oct. 20, 2006, "Modified Second Declaration Of Peter Sims" Before The Board Of Patent Appeals and Interferences, Interference No: 105,413.

Lentz Exhibit 1038 "First Declaration of George Fareed" Before The Board Of Patent Appeals and Interferences, Interference No: 105,413.

Lentz Exhibit 1039 "CV of Lawrence Sangermano" Before The Board Of Patent Appeals and Interferences, Interference No: 105,413.

Lentz Exhibit 1040, Filed Oct. 20, 2006, "Howell's Conception Documents" Before The Board Of Patent Appeals and Interferences, Interference No: 105,413.

Lentz Exhibit 1041 "Memorandum prepared by Lawrence Sangermano and dated Sep. 23, 1993" Before The Board Of Patent Appeals and Interferences, Interference No: 105,413.

Lentz Exhibit 1042 "First Declaration of Lawrence Sangermano" Before the Before The Board Of Patent Appeals and Interferences, Interference No: 105,413.

Lentz Exhibit 1043, Filed Oct. 20, 2006, "Harlow et al., Antibodies, A Laboratory Manual, Chapter 13, "Immunoaffinity Purification," pp. 511-552, 1988" Before The Board Of Patent Appeals and Interferences, Interference No: 105,413.

Lentz Exhibit 1044, Filed Oct. 20, 2006, "Cytologic: Unleash™ Immunotherapy" Before The Board Of Patent Appeals and Interferences, Interference No: 105,413.

Lentz Exhibit 1045, Filed Oct. 20, 2006, "Cytologic: Unleash™ Immunotherapy" Before The Board Of Patent Appeals and Interferences, Interference No: 105,413.

Lentz Exhibit 1046, Filed Oct. 20, 2006, "Comparison Chart Between Claims 42-46 And The Specification Of The '307 Application" Before The Board Of Patent Appeals and Interferences, Interference No: 105,413.

Lentz Exhibit 1047, Filed Oct. 20, 2006, "Petition to Enter a Plea of Guilty in *United States of America* v. *Meredith Rigdon Lentz* Case No. 3:05-00046 filed Jan. 6, 2006" Before The Board Of Patent Appeals and Interferences, Interference No: 105,413.

Lentz Exhibit 1048, Filed Oct. 20, 2006, "Judgment in a Criminal Case in *United States of America* v. *Meredith Rigdon Lentz* Case No. 3:05-00046 filed Jan. 13, 2006" Before The Board Of Patent Appeals and Interferences, Interference No: 105,413.

Lentz Exhibit 1049, Filed Oct. 20, 2006, "Motion to Modify, Amend, or Vacate Judgment in *United States of America* v. *Meredith Rigdon Lentz* Case No. 3:05-00046 filed Jan. 20, 2006" Before The Board Of Patent Appeals and Interferences, Interference No: 105,413.

Lentz Exhibit 1050, Filed Oct. 20, 2006, "Amended Judgment in *United States of America* v. *Meredith Rigdon Lentz* Case No. 3:05-00046 filed Feb. 15, 2006" Before The Board Of Patent Appeals and Interferences, Interference No: 105,413.

Lentz Exhibit 1051, Filed Oct. 20, 2006, "Deposition Transcript Of Peter J. Sims Taken Jun. 19, 2006 (With Errata Sheet)" Before The Board Of Patent Appeals and Interferences, Interference No: 105,413.

Lentz Exhibit 1052, Filed Oct. 20, 2006, "Engagement Letter of Dr. Donald J. Hillenbrand, M.D., by Bingham McCutchen, signed Feb. 7, 2006" Before The Board Of Patent Appeals and Interferences, Interference No: 105,413.

Lentz Exhibit 1053, Filed Oct. 20, 2006, "Pennica et al., Biochemistry 1992, 31, 1134-1141" Before The Board Of Patent Appeals and Interferences, Interference No: 105,413.

Lentz Exhibit 1054, Filed Oct. 20, 2006, "Pennica et al., Biochemistry 1993, 32, 3131-3138" Before The Board Of Patent Appeals and Interferences, Interference No: 105,413.

Lentz Exhibit 1055, Filed Oct. 20, 2006, "Third Declaration of Peter Sims" Before The Board Of Patent Appeals and Interferences, Interference No: 105,413.

Lentz Exhibit 1056, Filed Oct. 20, 2006, Venn Diagram Illustrating The Relationship Between "Stimulating" And "Enhancing" Before The Board Of Patent Appeals and Interferences, Interference No: 105,413.

Lentz Exhibit 1057, Filed Oct. 20, 2006, Venn Diagram Illustrating The Scope Of Claim 42 Of The Lentz '045 Application With Respect To "Enhancing an Immune Response" Before The Board Of Patent Appeals and Interferences, Interference No: 105,413.

Lentz Exhibit 1058, Filed Oct. 20, 2006, "CV Of Howard Bernstein" Before The Board Of Patent Appeals and Interferences, Interference No: 105,413.

Lentz Exhibit 1059, Filed Oct. 20, 2006, "Venn Diagram Illustrating The Embodiments Described At p. 6, Lines 13-16 Of The Lentz '045 Application" Before The Board Of Patent Appeals and Interferences, Interference No: 105,413.

Lentz Exhibit 1060, Filed Oct. 20, 2006, "Fourth Declaration of Peter Sims" Before The Board Of Patent Appeals and Interferences, Interference No: 105,413.

Lentz Exhibit 1061, Filed Oct. 20, 2006, "Declaration Of Howard Bernstein" Before The Board Of Patent Appeals and Interferences, Interference No: 105,413.

Lentz Exhibit 1062, Filed Oct. 20, 2006, "Deposition Transcript Of Prof. Peter Sims Taken Aug. 10, 2006" Before The Board Of Patent Appeals and Interferences, Interference No: 105,413.

Lentz Exhibit 1063, Filed Oct. 20, 2006, "C.V. Of Patrea L. Pabst" Before The Board Of Patent Appeals and Interferences, Interference No: 105,413.

Lentz Exhibit 1064, Filed Oct. 20, 2006, "A Letter From Patrea L. Pabst Sent To Rigdon Lentz Dated Jun. 3, 1998" Before The Board Of Patent Appeals and Interferences, Interference No: 105,413.

Lentz Exhibit 1065, Filed Oct. 20, 2006, "A Letter From Patrea L. Pabst Sent to Rigdon Lentz Dated Jun. 3, 1999" Before The Board Of Patent Appeals and Interferences, Interference No: 105,413.

Lentz Exhibit 1066, Filed Oct. 20, 2006, "U.S. Patent 4,708,713 Issued Nov. 24; 1987" Before The Board Of Patent Appeals and Interferences, Interference No: 105,413.

Lentz Exhibit 1067, Filed Oct. 20, 2006, "U.S. Appl. No. 09/083,307" Before The Board Of Patent Appeals and Interferences, Interference No: 105,413.

Lentz Exhibit 1068, Filed Oct. 20, 2006, "Preliminary Amendment Filed Apr. 7, 1999 Filed In The '307 Application" Before The Board Of Patent Appeals and Interferences, Interference No: 105,413.

Lentz Exhibit 1069, filed Oct. 20, 2006, "Information Disclosure Statement Filed Jan. 27, 1999 in The '307 Application" Before The Board Of Patent Appeals and Interferences, Interference No: 105, 413.

Lentz Exhibit 1070, Filed Oct. 20, 2006, "Response Filed Sep. 23, 1999 In The '307 Application" Before The Board Of Patent Appeals and Interferences, Interference No: 105,413.

Lentz Exhibit 1071, Filed Oct. 20, 2006, "Office Action Mailed Jan. 4, 2000 In The '307 Application" Before The Board Of Patent Appeals and Interferences, Interference No: 105,413.

Lentz Exhibit 1072, Filed Oct. 20, 2006, "Appeal Filed on Jul. 12, 2000 In The '307 Application" Before The Board Of Patent Appeals and Interferences, Interference No: 105,413.

Lentz Exhibit 1073, Filed Oct. 20, 2006, "Amendment Filed Apr. 12, 2002 in the '307 Application" Before The Board Of Patent Appeals and Interferences, Interference No: 105,413.

Lentz Exhibit 1075, Filed Oct. 20, 2006, "Rejection Mailed Oct. 21, 2002 in the '307 Application" Before The Board Of Patent Appeals and Interferences, Interference No: 105,413.

Lentz Exhibit 1076, Filed Oct. 20, 2006, "Interview Summary Dated Jan. 29, 2003 in the '309" Before The Board Of Patent Appeals and Interferences, Interference No: 105,413.

Lentz Exhibit 1077, Filed Oct. 20, 2006, "Amendment Filed Jan. 27, 2003 in the '307 Application" Before The Board Of Patent Appeals and Interferences, Interference No: 105,413.

Lentz Exhibit 1078, Filed Oct. 20, 2006, "Notice of Allowance Mailed Apr. 21, 2003 In The '307 Application" Before The Board Of Patent Appeals and Interferences, Interference No: 105,413.

Lentz Exhibit 1079, Filed Oct. 20, 2006, "U.S. Appl. No. 09/316,226" Before The Board Of Patent Appeals and Interferences, Interference No: 105,413.

Lentz Exhibit 1080, Filed Oct. 20, 2006, "Information Disclosure Statement Filed Aug. 27, 1999 In The '226 Application" Before The Board Of Patent Appeals and Interferences, Interference No: 105,413.

Lentz Exhibit 1081, Filed Oct. 20, 2006, "Supplemental Information Disclosure Statement Filed Fev. 2, 2000 In The '226 Application" Before The Board Of Patent Appeals and Interferences, Interference No: 105,413.

Lentz Exhibit 1082, Filed Oct. 20, 2006, "Office Action Mailed Feb. 14, 2000 in the '206 Application" Before The Board Of Patent Appeals and Interferences, Interference No: 105,413.

Lentz Exhibit 1083, Filed Oct. 20, 2006, "Amendment Filed Jun. 14, 2000 in the '226 Application" Before The Board Of Patent Appeals and Interferences, Interference No: 105,413.

Lentz Exhibit 1084, Filed Oct. 20, 2006, "Declaration of Dr. Rigdon Lentz Filed Jun. 21, 2000 in the '226 Application" Before The Board Of Patent Appeals and Interferences, Interference No: 105,413.

Lentz Exhibit 1085, Filed Oct. 20, 2006, "Office Action Mailed Sep. 28, 2000 in the '226 Application" Before The Board Of Patent Appeals and Interferences, Interference No: 105,413.

Lentz Exhibit 1086, Filed Oct. 20, 2006, "Amendment Filed Nov. 30, 2000 in the '226 Application" Before The Board Of Patent Appeals and Interferences, Interference No: 105,413.

Lentz Exhibit 1087, Filed Oct. 20, 2006, "Notice of Allowance Mailed Jan. 9, 2001 in the '226 Application" Before The Board Of Patent Appeals and Interferences, Interference No: 105,413.

Lentz Exhibit 1088, Filed Oct. 20, 2006, "Decision Issued By The Board Of Patent Appeals And Interferences Mailed Feb. 12, 2002 in The '226 Application" Before The Board Of Patent Appeals and Interferences, Interference No: 105,413.

Lentz Exhibit 1089, Filed Oct. 20, 2006, "Appeal Filed On Jan. 27, 2003 in the '226 Application" Before The Board Of Patent Appeals and Interferences, Interference No: 105,413.

Lentz Exhibit 1090, Filed Oct. 20, 2006, "Office Action Mailed May 18, 1999 in the '307 Application" Before The Board Of Patent Appeals and Interferences, Interference No: 105,413.

Lentz Exhibit 1091, Filed Oct. 20, 2006, "Supplemental Notice of Allowance Mailed Jul. 16, 2003 in the '307 Application" Before The Board Of Patent Appeals and Interferences, Interference No: 105,413.

Lentz Exhibit 1092, Filed Oct. 20, 2006, "First Declaration Of Patrea L. Pabst, Esq." Before The Board Of Patent Appeals and Interferences, Interference No: 105,413.

Lentz Exhibit 1093, Filed Oct. 20, 2006, "Version Of Howell Exhibit 2054 With More Legible Figures" Before The Board Of Patent Appeals and Interferences, Interference No: 105,413.

Lentz Exhibit 1094, Filed Oct. 20, 2006, "Bernstein Invoice dated Aug. 16, 2006 covering Jul. 18-Aug. 15, 2006" Before The Board Of Patent Appeals and Interferences, Interference No: 105,413.

Lentz Exhibit 1095, Filed Oct. 20, 2006, "Sims deposition transcript dated Sep. 7, 2006" Before The Board Of Patent Appeals and Interferences, Interference No: 105,413.

Lentz Exhibit 1096, Filed Oct. 20, 2006, "Bernstein's deposition transcript dated Sep. 6, 2006" Before The Board Of Patent Appeals and Interferences, Interference No: 105,413.

Lentz Exhibit 1097, Filed Dec. 22, 2006, "Maruyama, M., et al. Cell. 48 (1987) 343-350" Before The Board Of Patent Appeals and Interferences, Interference No: 105,413.

Lentz Exhibit 1098, Filed Dec. 22, 2006, "Fifth Declaration of Peter Sims" Before The Board Of Patent Appeals and Interferences, Interference No: 105,413.

Lentz Exhibit 1099, Filed Dec. 22, 2006, "Declaration of Prof. Hans Wigzell" Before The Board Of Patent Appeals and Interferences, Interference No: 105,413.

Lentz Exhibit 1100, Filed Dec. 22, 2006, "Examiner's Amendment mailed Jul. 8, 2005 in the Lentz '045 application" Before The Board Of Patent Appeals and Interferences, Interference No: 105,413.

Lentz Exhibit 1101, Filed Dec. 22, 2006, "Amendment and Response mailed on Oct. 23, 2001 in Howell U.S. Appl. No. 09/444,144 now U.S. Patent No. 6,379,708" Before The Board Of Patent Appeals and Interferences, Interference No: 105,413.

Lentz Exhibit 1102, Filed Dec, 22, 2006, "Information Disclosure Statement mailed on Oct. 23, 2001, Howell U.S. Appl. No. 09/444,144 now U.S. Patent No. 6,379,708" Before The Board Of Patent Appeals and Interferences, Interferences No: 105,413.

Lentz Exhibit 1103, Filed Dec. 22, 2006, "PTO Form 892 mailed Jan. 10, 2002 in Howell U.S. Appl. No. 09/444,144 now U.S. Patent No. 6,379,708" Before The Board Of Patent Appeals and Interferences, Interference No: 105,413.

Lentz Exhibit 1104, Filed Oct. 2, 2007, "Selinsky and Howell (2000) "Soluble Tumor Necrosis Factor Receptor Type I Enhances Tumor Development and Persistence in Vivo," Cellular Immunology 200:81-87 (also filed as Howell Exhibit 2075)" Before The Board Of Patent Appeals and Interferences, Interference No: 105,413.

Lentz Exhibit 1105, Filed Oct. 2, 2007, "Letter dated Apr. 9, 1998 from Patrea L. Pabst to Dr. M. Rigdon Lentz transmitting draft of U.S. Appl. No. 09/709,045 [sic] (U.S. Appl. No. 09/083,307)" Before The Board Of Patent Appeals and Interferences, Interference No: 105,413.

Lentz Exhibit 1106, Filed Oct. 2, 2007, "Draft of U.S. Appl. No. 09/709,045 [sic] (U.S. Appl. No. 09/083,307) faxed from Patrea L. Pabst to Dr. M. Rigdon Lentz on Apr. 9, 1998 and facsimile confirmation page." Before The Board Of Patent Appeals and Interferences, Interference No: 105,413.

Lentz Exhibit 1107, Filed Oct. 2, 2007, "Facsimile confirmation of transmittal of draft of patent application U.S. Appl. No. 09/709,045 [sic] (U.S. Appl. No. 09/083,307) sent from Patrea L. Pabst to Dr. M. Rigdon Lentz on Apr. 20, 1998" Before The Board Of Patent Appeals and Interferences, Interference No: 105,413.

Lentz Exhibit 1108, Filed Oct. 2, 2007, "Letter, fax cover page and marked-up draft of patent U.S. Appl. No. 09/709,045 [sic] (U.S. Appl. No. 09/083,307) from Dr. M. Rigdon Lentz to Patrea L. Pabst dated Apr. 20, 1998" Before The Board Of Patent Appeals and Interferences, Interference No: 105,413.

Lentz Exhibit 1109, Filed Oct. 2, 2007, "Letter, fax cover page, fax confirmation and revised draft of U.S. Appl. No. 09/709,045 [sic] (U.S. Appl. No. 09/083,307) from Patrea L. Pabst to Dr. M. Rigdon Lentz dated Apr. 30, 1998" Before The Board Of Patent Appeals and Interferences, Interference No: 105,413.

Lentz Exhibit 1110, Filed Oct. 2, 2007, "Letter from Dr. M. Rigdon Lentz dated May 2, 1998 and transmitted via facsimile on May 7, 1998 to Patrea L. Pabst containing comments and examples to include in U.S. Appl. No. 09/709,045 [sic] (U.S. Appl. No. 09/083,307)" Before The Board Of Patent Appeals and Interferences, Interference No: 105,413.

Lentz Exhibit 1111, Filed Oct. 2, 2007, "Fax cover sheet transmitting revised draft of U.S. Appl. No. 09/709,045 [sic] (U.S. Appl. No. 09/083,307) from Patrea L. Pabst to M. Rigdon Lentz dated May 11, 1998" Before The Board Of Patent Appeals and Interferences, Interference No: 105,413.

Lentz Exhibit 1112, Filed Oct. 2, 2007, "Letter from Patrea L. Pabst to Dr. M. Rigdon Lentz transmitting revised draft of U.S. Appl. No. 09/709,045 [sic] (U.S. Appl. No. 09/083,307) on May 11, 1998 including a copy of Sender's Receipt from Federal Express" Before The Board Of Patent Appeals and Interferences, Interference No: 105,413.

Lentz Exhibit 1113, Filed Oct. 2, 2007, "Patent docket for Patrea L. Pabst from May 11, 1998 to May 22, 1998" Before The Board Of Patent Appeals and Interferences, Interference No: 105,413.

Lentz Exhibit 1114 "(part 1) Deposition transcript of Mark D. Howell, Ph.D. taken Apr. 5, 2007; (part 2) Confidential portion of Deposition of Mark D. Howell, Ph.D." Before The Board Of Patent Appeals and Interferences, Interference No: 105,413.

Lentz Exhibit 1115, Filed Oct. 2, 2007, "Deposition transcript of Cheryl L. Selinsky, Ph.D. taken Apr. 6, 2007" Before The Board Of Patent Appeals and Interferences, Interference No: 105,413.

Lentz Exhibit 1116, Filed Oct. 2, 2007, "Second Declaration of Patrea L. Pabst" Before The Board Of Patent Appeals and Interferences, Interference No: 105,413.

Lentz Exhibit 1117, Filed Oct. 2, 2007, "1997 Draft Business Plan [sic] (Confidential Private Placement Memorandum for Immutherapeutics, Inc.)" Before The Board Of Patent Appeals and Interferences, Interference No: 105,413.

Lentz Exhibit 1118, Filed Oct. 2, 2007, "Redacted draft manuscript sent by Mrs. Jennifer Lentz on Jul. 26, 1998" Before The Board Of Patent Appeals and Interferences, Interference No: 105,413.

Lentz Exhibit 1119, Filed Oct. 2, 2007, "National Cancer Institute FactSheet (Aug. 16, 2004)" Before The Board Of Patent Appeals and Interferences, Interference No: 105,413.

Lentz Exhibit 1120, Filed Oct. 2, 2007, "Kaminska, et al. Tumour Biol. Jul-Aug. 2005;26(4):186-94" Before The Board Of Patent Appeals and Interferences, Interference No: 105,413.

Lentz Exhibit 1121, Filed Oct. 2, 2007, "Warzocha, et al. J Clin Oncol. Feb. 1997;15(2):499-508" Before The Board Of Patent Appeals and Interferences, Interference No: 105,413.

Lentz Exhibit 1122, Filed Oct. 2, 2007, "Kaminska, et al. Oncology. 2006;70(2):115-25" Before The Board Of Patent Appeals and Interferences, Interference No: 105,413.

Lentz Exhibit 1123, Filed Oct. 2, 2007, "Third Declaration of Patrea L. Pabst" Before The Board Of Patent Appeals and Interferences, Interference No. 105,413.

Lentz Exhibit 1124, Filed Oct. 2, 2007, "Transmittal Page from Ex. 1118" Before The Board Of Patent Appeals and Interferences, Interference No: 105,413.

Lentz Exhibit 1125, Filed Oct. 2, 2007, "Gatanaga et al. Lymphokine Research. 1990, 9(2):225-229" Before The Board Of Patent Appeals and Interferences, Interference No: 105,413.

Lentz Exhibit 1126, Filed Oct. 2, 2007, "Schall, T. J., et al. Cell 1990, 61, 361-70" Before The Board Of Patent Appeals and Interferences, Interference No: 105,413.

Lentz Exhibit 1127, Filed Oct. 2, 2007, "Second Declaration of Prof. Hans Wigzell" Before The Board Of Patent Appeals and Interferences, Interference No: 105,413.

Lentz Exhibit 1128, Filed Oct. 2, 2007, "Declaration of Jeffrey S. Muir" Before The Board Of Patent Appeals and Interferences, Interference No: 105,413.

Lentz Exhibit 1129, Filed Oct. 2, 2007, "Materials from KPMG" Before The Board Of Patent Appeals and Interferences, Interference No: 105,413.

Lentz Exhibit 1130 "Fourth Declaration of Ms. Patrea Pabst" Before The Board Of Patent Appeals and Interferences, Interference No: 105,413.

Lentz Exhibit 1131, Filed Oct. 2, 2007, "Email from Mrs. Jennifer Lentz to Mr. Jeffrey Muir Dated May 14, 2002" Before The Board Of Patent Appeals and Interferences, Interference No: 105,413.
Lentz Exhibit 1132, Filed Oct. 2, 2007, "Email from Mrs. Jennifer Lentz to Mr. Jeffrey Muir Dated Jul. 18, 2002" Before The Board Of Patent Appeals and Interferences, Interference No: 105,413.
Lentz Exhibit 1133, Filed Oct. 2, 2007, "Email from Mrs. Jennifer Lentz to Mr. Jeffrey Muir Dated Aug. 22, 2002" Before The Board Of Patent Appeals and Interferences, Interference No: 105,413.
"Appearance Record Nov. 20, 2007" Before The Board Of Patent Appeals and Interferences, Interference No: 105,413.
"Appearance Record Nov. 9, 2006" Before The Board Of Patent Appeals and Interferences, Interference No: 105,413.
"Argument On Behalf Of Junior Party Howell; Argument On Behalf Of Senior Party Lentz; Rebuttal Argument On Behalf Of Junior Party Howell; Rebuttal Argument On Behalf Of Senior Party Lentz Nov. 9, 2006" Before The Board Of Patent Appeals and Interferences, Interference No: 105,413.
"Corrected Status Of Related U.S. Appl. No. 09/699,003 Nov. 27, 2007" Before The Board Of Patent Appeals and Interferences, Interference No: 105,413.
"Decision - Interlocutory Motion - Bd.R. 121 Dec. 18, 2007" Before The Board Of Patent Appeals and Interferences, Interference No: 105,413.
"Decision—Interlocutory Motion - Bd.R. 123(B) Jan. 23, 2008" Before The Board Of Patent Appeals and Interferences, Interference No: 105,413.
"Decision—Interlocutory Motion - Bd.R. 123(B) Jan. 9, 2008" Before The Board Of Patent Appeals and Interferences, Interference No: 105,413.
"Decision—Interlocutory Motion - Bd.R. 123(B) May 22, 2007" Before The Board Of Patent Appeals and Interferences, Interference No: 105,413.
"Decision—Priority—Bd.R. 125(A) Jan. 9, 2008" Before The Board Of Patent Appeals and Interferences, Interference No: 105,413.
"Decision—Rehearing - Bd.R 125(C) Sep. 7, 2006" Before The Board Of Patent Appeals and Interferences, Interference No: 105,413.
"Decision On Motion- Bd.R 121 Dec. 7, 2006" Before The Board Of Patent Appeals and Interferences, Interference No: 105,413.
"Decision On Motions Jan. 25, 2007" Before The Board Of Patent Appeals and Interferences, Interference No: 105,413.
"Declaration Standing Order With Attachments Jan. 12, 2006" Before The Board Of Patent Appeals and Interferences, Interference No: 105,413.
"Denial Of Request for Rehearing Apr. 7, 2008" Before The Board Of Patent Appeals and Interferences, Interference No: 105,413.
"Deposition of Leland Charles Leber Apr. 4, 2007" Before The Board Of Patent Appeals and Interferences, Interference No: 105,413.
"Erratum Nov. 14, 2007" Before The Board Of Patent Appeals and Interferences, Interference No: 105,413.
"Howell Contingent Substantive Motion 4 (Attacking Accorded Benefit Of U.S. Appl. No. 09/083,307 to Lentz) Apr. 18, 2006" Before The Board Of Patent Appeals and Interferences, Interference No: 105,413.
"Howell Demonstratives 1-25 Oral Hearing Nov. 9, 2006" Before The Board Of Patent Appeals and Interferences, Interference No: 105,413.
"Howell Exhibit List As Of Apr. 18, 2006" Before The Board Of Patent Appeals and Interferences, Interference No: 105,413.
"Howell Exhibit List As Of Aug. 18, 2006" Before The Board Of Patent Appeals and Interferences, Interference No: 105,413.
"Howell Exhibit List As Of Feb. 21, 2006" Before The Board Of Patent Appeals and Interferences, Interference No: 105,413.
"Howell Exhibit List As Of Jul. 10, 2007" Before The Board Of Patent Appeals and Interferences, Interference No: 105,413.
"Howell Exhibit List As Of Jul. 18, 2006" Before The Board Of Patent Appeals and Interferences, Interference No: 105,413.
"Howell Exhibit List As Of Jul. 7, 2006" Before The Board Of Patent Appeals and Interferences, Interference No: 105,413.
"Howell Exhibit List As Of Mar. 12, 2007" Before The Board Of Patent Appeals and Interferences, Interference No: 105,413.
"Howell Exhibit List As Of May 18, 2007" Before The Board Of Patent Appeals and Interferences, Interference No: 105,413.
"Howell Exhibit List As Of Oct. 2, 2007" Before The Board Of Patent Appeals and Interferences, Interference No: 105,413.
"Howell Exhibit List As Of Oct. 24,2006" Before The Board Of Patent Appeals and Interferences, Interference No: 105,413.
"Howell Identification Of Lead and Back-Up Counsel Jan. 26, 2006" Before The Board Of Patent Appeals and Interferences, Interference No: 1 05,413.
"Howell Identification Of Real Parties In Interest Jan. 26, 2006" Before The Board Of Patent Appeals and Interferences, Interference No: 1 05,413.
"Howell Identification Of Lead And Back-Up Counsel Nov. 26, 2008" Before The Board Of Patent Appeals and Interferences, Interference No: 1 05,413.
"Howell List Of Proposed Motions Mar. 14, 2006" Before The Board Of Patent Appeals and Interferences, Interference No: 105,413.
"Howell Miscellaneous Motion 6 (Seeking Additional Discovery) May 18, 2007" Before The Board Of Patent Appeals and Interferences, Interference No: 105,413.
"Howell Modified Opposition 1 (Opposing Lentz's Request to Substitute Claims 42-46 Into The '045 Application Jul. 18, 2006" Before The Board Of Patent Appeals and Interferences, Interference No: 105,413.
"Howell Notice of Change of Address Of Lead and Back-Up Counsel Mar. 23, 2006" Before The Board Of Patent Appeals and Interferences, Interference No: 105,413.
"Howell Notice Of Filing Priority Statement Apr. 18, 2006" Before The Board Of Patent Appeals and Interferences, Interference No: 105,413.
"Howell Notice Of Judicial Review Jun. 26,2008" Before The Board Of Patent Appeals and Interferences, Interference No: 105,413.
"Howell Notice Of Non-Receipt Of File Copies Feb. 17, 2006" Before The Board Of Patent Appeals and Interferences, Interference No: 1 05,413.
"Howell Notice Of Related Proceedings Jan. 26, 2006" Before The Board Of Patent Appeals and Interferences, Interference No: 1 05,413.
"Howell Notice Of Service Of Requested Documents Feb. 21, 2006" Before The Board Of Patent Appeals and Interferences, Interference No: 105,413.
"Howell Observations on Cross-Examination Of Dr. Bernstein Sep. 19, 2006" Before The Board Of Patent Appeals and Interferences, Interference No: 1 05,413.
"Howell Opposition 1 (Opposing Lentz's Request To Substitute Claims 42-46 Into The '045 Application) Jul. 7, 2006" Before The Board Of Patent Appeals and Interferences, Interference No: 1 05,413.
"Howell Opposition 2 (Opposing Lentz's Request for Benefit of U.S. Appl. No. 60/164,695) Jul. 7,2006" Before The Board Of Patent Appeals and Interferences, Interference No: 1 05,413.
"Howell Opposition 3 (Opposing Lentz's Assertion That U.S.P.N. 6,379,708 Is Obvious Under 35 U.S.C. § 103) Jul. 7, 2006" Before The Board Of Patent Appeals and Interferences, Interference No: 105,413.
"Howell Opposition To Lentz Priority Motion May 29, 2007" Before The Board Of Patent Appeals and Interferences, Interference No: 105,413.
"Howell Preliminary Motion 5 (Lentz Claims 23-27 and 32-41 Are Unpatentable Under 35 U.S.0 §§ 1 02(B)/1 03) Dec. 4, 2006" Before The Board Of Patent Appeals and Interferences, Interference No: 105,413.
"Howell Priority Motion Mar. 12, 2007" Before The Board Of Patent Appeals and Interferences, Interference No: 105,413.
"Howell Priority Reply Jul. 10, 2007" Before The Board Of Patent Appeals and Interferences, Interference No: 105,413.
"Howell Priority Statement Apr. 18, 2006" Before The Board Of Patent Appeals and Interferences, Interference No: 105,413.
"Howell Reply 3 (Attacking Accorded Benefit Of U.S. Appl. No. 09/699,003 and U.S. Appl. No. 09/316,226 to Lentz) Aug. 18, 2006" Before The Board Of Patent Appeals and Interferences, Interference No: 105,413.

"Howell Reply 4 (Attacking Accorded Benefit of U.S. Appl. No. 09/083,307 to Lentz) Aug. 18, 2006" Before The Board Of Patent Appeals and Interferences, Interference No: 105,413.
"Howell Request for Documents Feb. 2, 2006" Before The Board Of Patent Appeals and Interferences, Interference No: 105,413.
"Howell Request for File Copies Jan. 26, 2006" Before The Board Of Patent Appeals and Interferences, Interference No: 105,413.
"Howell Request for Missing Documents Mar. 14, 2006" Before The Board Of Patent Appeals and Interferences, Interference No: 105,413.
"Howell Request for Oral Argument Aug. 21, 2007" Before The Board Of Patent Appeals and Interferences, Interference No: 105,413.
"Howell Request for Oral Argument Sep. 19, 2006" Before The Board Of Patent Appeals and Interferences, Interference No: 105,413.
"Howell Request for Rehearing Feb. 8, 2008" Before The Board Of Patent Appeals and Interferences, Interference No: 105,413.
"Howell Sub. Of Power of Attorney Nov. 26, 2008" Before The Board Of Patent Appeals and Interferences, Interference No: 105,413.
"Howell Submission Of Annotated Claims Feb. 9, 2006" Before The Board Of Patent Appeals and Interferences, Interference No: 105,413.
"Howell Submission Of Clean Claims Jan. 26, 2006" Before The Board Of Patent Appeals and Interferences, Interference No: 105,413.
"Howell Submission Of Powers Of Attorney Jan. 26, 2006" Before The Board Of Patent Appeals and Interferences, Interference No: 105,413.
"Howell Submission Of Record Oct. 2, 2006" Before The Board Of Patent Appeals and Interferences, Interference No: 105,413.
"Howell Substantive Motion 1 Feb. 21, 2006" Before The Board Of Patent Appeals and Interferences, Interference No: 105,413.
"Howell Substantive Motion 2 Feb. 21, 2006" Before The Board Of Patent Appeals and Interferences, Interference No: 105,413.
"Howell Substantive Motion 3 (Attacking Accorded Benefit Of U.S. Appl. No. 09/699,003 and U.S. Appl. No. 09/316,226 to Lentz) Apr. 18, 2006" Before The Board Of Patent Appeals and Interferences, Interference No: 105,413.
"Judgment - Merits - Bd.R 127 Jan. 9, 2008" Before The Board Of Patent Appeals and Interferences, Interference No: 105,413.
"Lentz 37 Cfr 41.157(C)(4) Notice Of Deposition Of Peter Sims Dec. 31, 2006" Before The Board Of Patent Appeals and Interferences, Interference No: 105,413.
"Lentz Clean Claims Jan. 19, 2006" Before The Board Of Patent Appeals and Interferences, Interference No: 105,413.
"Lentz Comments Regarding Annotated Claims Feb. 1, 2006" Before The Board Of Patent Appeals and Interferences, Interference No: 105,413.
"Lentz Exhibit List (As Of May 9, 2006)" Before The Board Of Patent Appeals and Interferences, Interference No: 105,413.
"Lentz Exhibit List (As Of Apr. 18, 2006)" Before The Board Of Patent Appeals and Interferences, Interference No: 105,413.
"Lentz Exhibit List (As Of Aug. 18, 2006)" Before The Board Of Patent Appeals and Interferences, Interference No: 105,413.
"Lentz Exhibit List (As Of Dec. 22, 2006)" Before The Board Of Patent Appeals and Interferences, Interference No: 105,413.
"Lentz Exhibit List (As Of Jul. 10, 2007)" Before The Board Of Patent Appeals and Interferences, Interference No: 1 05,413.
"Lentz Exhibit List (As Of Jul. 7, 2006)" Before The Board Of Patent Appeals and Interferences, Interference No: 105,413.
"Lentz Exhibit List (As Of Oct. 18, 2006)" Before The Board Of Patent Appeals and Interferences, Interference No: 105,413.
"Lentz Exhibit List (As Of Oct. 2, 2007)" Before The Board Of Patent Appeals and Interferences, Interference No: 105,413.
"Lentz List of Proposed Motions Mar. 14, 2006" Before The Board Of Patent Appeals and Interferences, Interference No: 105,413.
"Lentz Miscellaneous Motion 4 (Request For Withdrawal Pursuant To 37 Cfr 1 OAO(C)(5)) Nov. 29, 2006" Before The Board Of Patent Appeals and Interferences, Interference No: 1 05,413.
"Lentz Modified Motion 2 May 9, 2006" Before The Board Of Patent Appeals and Interferences, Interference No: 105,413.
"Lentz Motion 1 Mar. 7, 2006" Before The Board Of Patent Appeals and Interferences, Interference No: 105,413.
"Lentz Motion 2 Apr. 18, 2006" Before The Board Of Patent Appeals and Interferences, Interference No: 105,413.
"Lentz Motion 3 May 9, 2006" Before The Board Of Patent Appeals and Interferences, Interference No: 105,413.
"Lentz Notice Of Change Of Lead Counsel Oct. 4, 2006" Before The Board Of Patent Appeals and Interferences, Interference No: 1 05,413.
"Lentz Notice Of Deposition (Cheryl Lynn Selinsky) Mar. 30, 2007" Before The Board Of Patent Appeals and Interferences, Interference No: 105,413.
"Lentz Notice Of Deposition (Donald Hillebrand) Apr. 3, 2007" Before The Board Of Patent Appeals and Interferences, Interference No: 105,413.
"Lentz Notice Of Deposition (Leland Charles Leber) Mar. 29, 2007" Before The Board Of Patent Appeals and Interferences, Interference No: 105,413.
"Lentz Notice Of Deposition (Mark Douglas Howell) Mar. 30, 2007" Before The Board Of Patent Appeals and Interferences, Interference No: 105,413.
"Lentz Notice Of Related Proceedings Jan. 19, 2006" Before The Board Of Patent Appeals and Interferences, Interference No: 1 05,413.
"Lentz Notice Of Service Of Priority Statement Apr. 25, 2006" Before The Board Of Patent Appeals and Interferences, Interference No: 1 05,413.
"Lentz Opposition 3 Jul. 7, 2006" Before The Board Of Patent Appeals and Interferences, Interference No: 105,413.
"Lentz Opposition 4 Jul. 7, 2006" Before The Board Of Patent Appeals and Interferences, Interference No: 105,413.
"Lentz Opposition 5 Dec. 22, 2006" Before The Board Of Patent Appeals and Interferences, Interference No: 105,413.
"Lentz Opposition to Howell Priority Motion May 29, 2007" Before The Board Of Patent Appeals and Interferences, Interference No: 105,413.
"Lentz POA and Designation Of Back-Up Lead Attorneys Jan. 19, 2006" Before The Board Of Patent Appeals and Interferences, Interference No: 105,413.
"Lentz Priority Motion Apr. 23, 2007" Before The Board Of Patent Appeals and Interferences, Interference No: 105,413.
"Lentz Real Party In Interest Jan. 19, 2006" Before The Board Of Patent Appeals and Interferences, Interference No: 105,413.
"Lentz Reply 1 Aug. 18, 2006" Before The Board Of Patent Appeals and Interferences, Interference No: 105,413.
"Lentz Reply 2 Aug. 18, 2006" Before The Board Of Patent Appeals and Interferences, Interference No: 105,413.
"Lentz Reply 3 Apr. 23, 2007" Before The Board Of Patent Appeals and Interferences, Interference No: 105,413.
"Lentz Reply To Howell's Opposition To Lentz Priority Motion Jul. 10, 2007" Before The Board Of Patent Appeals and Interferences, Interference No: 105,413.
"Lentz Request File Copies Jan. 19, 2006" Before The Board Of Patent Appeals and Interferences, Interference No: 105,413.
"Lentz Request For Change Of Email Recipients Sep. 7, 2006" Before The Board Of Patent Appeals and Interferences, Interference No: 105,413.
"Lentz Request For Deletion Of Email Recipient Jul. 26, 2006" Before The Board Of Patent Appeals and Interferences, Interference No: 105,413.
"Lentz Request For Documents Feb. 1, 2006" Before The Board Of Patent Appeals and Interferences, Interference No: 105,413.
"Lentz Request For Oral Argument Aug. 21, 2007" Before The Board Of Patent Appeals and Interferences, Interference No: 105,413.
"Lentz Request For Oral Argument Sep. 19, 2006" Before The Board Of Patent Appeals and Interferences, Interference No: 105,413.
"Lentz Request For Panel Reconsideration Aug. 8, 2006" Before The Board Of Patent Appeals and Interferences, Interference No: 105,413.
"Lentz Responses To Howell Observations On Cross-Examination Of Dr Sims Oct. 10, 2006" Before The Board Of Patent Appeals and Interferences, Interference No: 105,413.

"Lentz Responses To Howell Observations On Cross-Examination Of Dr. Bernstein Oct. 10, 2006" Before The Board Of Patent Appeals and Interferences, Interference No: 105,413.
"Lentz Resubmitted List Of Exhibits Served/Filed With Motion 1 Jul. 5, 2007" Before The Board Of Patent Appeals and Interferences, Interference No: 105,413.
"Lentz Revised Exhibit List (As Of May 29, 2007)" Before The Board Of Patent Appeals and Interferences, Interference No: 105,413.
"Lentz Submission Of Demonstratives Nov. 12, 2007" Before The Board Of Patent Appeals and Interferences, Interference No: 105,413.
"Lentz Submission Of Demonstratives Nov. 2, 2006" Before The Board Of Patent Appeals and Interferences, Interference No: 105,413.
"Lentz Submission Of The Record (Priority Phase) Sep. 27, 2007" Before The Board Of Patent Appeals and Interferences, Interference No: 105,413.
"Lentz Submission Of The Record Oct. 20, 2006" Before The Board Of Patent Appeals and Interferences, Interference No: 105,413.
"Lentz Substitute Reply 3 Apr. 23, 2007" Before The Board Of Patent Appeals and Interferences, Interference No: 105,413.
"Lentz Updated Notice Of Lead And Backup Counsel Nov. 16, 2007" Before The Board Of Patent Appeals and Interferences, Interference No: 1 05,413.
"Lentz's List Of Exhibits Served/Filed With Motion 1 Mar. 7, 2006" Before The Board Of Patent Appeals and Interferences, Interference No: 1 05,413.
"Lentz's Notice Of Submission Of Priority Statement Apr. 18, 2006" Before The Board Of Patent Appeals and Interferences, Interference No: 1 05,413.
"Lentz's Corrected List Of Exhibits Served/Filed With Motion 1 Mar. 7 2006" Before The Board Of Patent Appeals and Interferences, Interference No: 1 05,413.
"Lentz's Response To Howell's Request For Documents Feb. 21, 2006" Before The Board Of Patent Appeals and Interferences, Interference No: 1 05,413.
"Lentz's Revised Opposition To Howell's Priority Motion Jun. 25, 2007" Before The Board Of Patent Appeals and Interferences, Interference No: 105,413.
"Notice Of Change In Schedule Jul. 27, 2006" Before The Board Of Patent Appeals and Interferences, Interference No: 105,413.
"Notice Of Change In Schedule May 8, 2006" Before The Board Of Patent Appeals and Interferences, Interference No: 105,413.
"Opinion (Order Admitting Pro Hac Vice - Bd.R 5(A)) Oct. 26, 2006" Before The Board Of Patent Appeals and Interferences, Interference No: 105,413.
"Oral Hearing Held: Nov. 20, 2007" Before The Board Of Patent Appeals and Interferences, Interference No: 1 05,413.
"Order - Authorizing Miscellaneous Motion - Bd.R. 123(B)(1 ) (Ii) May 15, 2007" Before The Board Of Patent Appeals and Interferences, Interference No: 105,413.
"Order - Authorizing Motion—Bd.R. 121 Nov. 9, 2006" Before The Board Of Patent Appeals and Interferences, Interference No: 105,413.
"Order - Expunging Paper - Bd.R. 7(A) Jan. 4, 2007" Before The Board Of Patent Appeals and Interferences, Interference No: 105,413.
"Order - Expunging Paper - Bd.R. 7(A) Mar. 26, 2008" Before The Board Of Patent Appeals and Interferences, Interference No: 105,413.
"Order - Expunging Paper - Bd.R. 7(A) May 2, 2006" Before The Board Of Patent Appeals and Interferences, Interference No: 1 05,413.
"Order - Expunging Paper -Bd.R. 7 Sep. 11, 2007" Before The Board Of Patent Appeals and Interferences, Interference No: 105,413.
"Order - Miscellaneous - Bd.R 104(A) May 5, 2006" Before The Board Of Patent Appeals and Interferences, Interference No: 105,413.
"Order - Miscellaneous—Bd.R 104(a) Nov. 30, 2006" Before The Board Of Patent Appeals and Interferences, Interference No: 105,413.
"Order - Miscellaneous—Bd.R 104(a) Oct. 4, 2006" Before The Board Of Patent Appeals and Interferences, Interference No: 105,413.
"Order - Miscellaneous - Bd.R 1 04(A) Sep. 8, 2006" Before The Board Of Patent Appeals and Interferences, Interference No: 105,413.
"Order - Miscellaneous- Bd.R. 1 04(A) Apr. 20, 2007" Before The Board Of Patent Appeals and Interferences, Interference No: 105,413.
"Order - Motion Times - Bd.R. 104(C) Mar. 29, 2006" Before The Board Of Patent Appeals and Interferences, Interference No: 105,413.
"Order - Oral Argument - Bd.R. 124 Sep. 12, 2007" Before The Board Of Patent Appeals and Interferences, Interference No: 105,413.
"Order - Oral Argument - Bd.R. 124 Sep. 27, 2006" Before The Board Of Patent Appeals and Interferences, Interference No: 105,413.
"Order - Priority Times - Bd.R 104(C) Jan. 25, 2007" Before The Board Of Patent Appeals and Interferences, Interference No: 105,413.
"Order Authorizing Copies Of Office Records Jan. 27,2006" Before The Board Of Patent Appeals and Interferences, Interference No: 105,413.
"Order Authorizing Motions Feb. 7, 2006" Before The Board Of Patent Appeals and Interferences, Interference No: 105,413.
"Order Authorizing Motions Mar. 1, 2006" Before The Board Of Patent Appeals and Interferences. Interference No: 105,413.
"Order -Miscellaneous-Bd.R. 104(A) Jul. 25, 2006" Before The Board Of Patent Appeals and Interferences, Interference No: 105,413.
"Order-Miscellaneous-Bd.R 104(A) Jul. 14, 2006" Before The Board Of Patent Appeals and Interferences, Interference No: 105,413.
"Revised Lentz Motion 3 May 9, 2006" Before The Board Of Patent Appeals and Interferences, Interference No: 105,413.
"Status Of Related Application U.S. Appl. No. 09/699,003 Nov. 26, 2007" Before The Board Of Patent Appeals and Interferences, Interference No: 105,413.
"Status Update For U.S. Appl. No. 09/699,003 Dec. 21, 2007" Before The Board Of Patent Appeals and Interferences, Interference No: 105,413.
"Status Update For U.S. Appl. No. 09/699.003 Jan. 7, 2008" Before The Board Of Patent Appeals and Interferences, Interference No: 105,413.
"Submission Of Transcript Of Leland Charles Leber Deposition May 4, 2007" Before The Board Of Patent Appeals and Interferences, Interference No: 105,413.
"Transmittal Of Lentz's Revised Exhibit List (As Of May 29, 2007)" Before The Board Of Patent Appeals and Interferences, Interference No: 105,413.
"Transmittal Of Lentz's Revised Opposition To Howell's Priority Motion Jun. 25, 2007" Before The Board Of Patent Appeals and Interferences, Interference No: 105,413.
"Howell Observations On Cross-Examination Of Dr. Sims Sep. 19, 2006" Before The Board Of Patent Appeals and Interferences, Interference No: 105,413.
U.S. Appl. No. 12/685,307, published Jun. 19, 2008, Lentz.
Ammirati et al., "Detection of TNF inhibitors (soluble receptors) in the sera and tumor cyst fluid of patients with malignant astrocytomas of the brain" Front Biosci Oct 1;6:B17-24 (2001).
Burger et al., "Association between serum levels of soluble tumor necrosis factor receptors/CA 125 and disease progression in patients with epithelial ovarian malignancy: a gynecologic oncology group study" Cancer 101(1):106-15 (2004).
Chen et al., "Experimental vaccine strategies for cancer immunotherapy" J Biomed Sci 5(4):231-52 (1998).
Csehi et al. "Tumor necrosis factor (TNF) interferes with insulin signaling through the p55 TNF receptor death domain." Biochem Biophys Res Commun. Apr. 1, 2005;329(1):397-405.
Eisen, "General Immunology", J.B. Lippincott Company, 78 (1980).
Feng, "Regulatory roles and molecular signaling of TNF family members in osteoclasts." Gene. Apr 25, 2005;350(1):1-13.

Gonzalez et al., "A novel cancer vaccine composed of human-recombinant epidermal growth factor linked to a carrier protein: report of a pilot clinical trial" Ann Oncol 9(4):431-5 (1998).

Holtmann et al. "The emerging distinct role of TNF-receptor 2 (p80) signaling in chronic inflammatory disorders." Arch Immunol Ther Exp (Warsz). 2002;50(4):279-88.

Kircheis et al., "Cytokine gene-modified tumor cells for prophylactic and therapeutic vaccination: IL-2, IFN-gamma, or combination IL-2 + IFN-gamma" Cytokines Cell Moll Ther 4(2)2:95-103 (1998).

"Laboratory Filtration Concepts," Pall Life Sciences, http://www.pall/corn/catalogs/filterbook/concepts.asp, retrieved Apr. 12, 2002.

Liu et al. "Molecular mechanism of TNF signaling and beyond." Cell Res. 2005 Jan;15(1):24-7.

Mack et al., "Five-year results of a phase II study with low-dose bacille Calmette-Guerin therapy in high-risk superficial bladder cancer" Urology 45(6):958-61 (1995).

Maier et al., "Physiological levels of pro- and anti-inflammatory mediators in cerebrospinal fluid and plasma: a normative study" J Neurotrauma 22(7):822-35 (2005).

Moller et al., "Vaccination with IL-7 gene-modified autologous melanoma cells can enhance the anti-melanoma lytic activity in peripheral blood of patients with a good clinical performance status: a clinical phase I study" Br J Cancer 77(11):1907-16 (1998).

Mordoh et al. "Allogeneic cells vaccine increases disease-free survival in stage III melanoma patients. A non randomized phase II study" Medicina (B Aires) 57(4)4:421-7 (1997).

Moviglia "Development of tumor B-cell lymphocyte hybridoma (TBH) autovaccination. Results of phase I-II clinical trial" Transfus Sci 17(4):643-9 (1996).

Muc-Wierzgon et al. "Circadian fluctuations of melatonin, tumor necrosis factor-alpha and its soluble receptors in the circulation of patients with advanced gastrointestinal cancer" J Exp Clin Cancer Res. 2003 Jun;22(2):171-8.

Rzymski et al. "Serum tumor necrosis factor alpha receptors p55/p75 ratio and ovarian cancer detection." Int J Gynaecol Obstet. 2005 Mar;88(3):292-8.

Sasaki et al., "Identification of a soluble GM-CSF binding protein in the supernatant of a human choriocarcinoma cell line," Biochem. Biophys. Res. Commun. 183(1):252-257 (1992). (Abstract Only).

Serwin et al. "[Soluble tumor-necrosis-factor-alpha receptor type-1 as a marker of activity of psoriasis vulgaris and effects of its treatment]" Przegl Lek. 2005;62(2):95-7.

Serwin et al. "Soluble tumor necrosis factor alpha receptor type 1 in psoriasis patients treated with narrowband ultraviolet B" Photodermatol Photoimmunol Photomed. Aug. 2005;21(4):210-1.

Shai et al. "A prospective study of soluble tumor necrosis factor-alpha receptor II (sTNF-RII) and risk of coronary heart disease among women with type 2 diabetes." Diabetes Care. Jun. 2005;28(6):1376-82.

Sinclair, "Filtration Fundamentals: Is Knowledge Of Filter Technology Something You Let Fall Through The Cracks?" The Scientist 12[19]:18 (1998), http://www.the-scientist.com/yr1998/sept/profile1_980928.html, retrieved on Apr. 12, 2002.

Sivanandham et al., "Colon cancer cell vaccine prepared with replication-deficient vaccinia viruses encoding B7.1 and interleukin-2 induce antitumor response in syngeneic mice" Cancer Immunol Immunother 46(5):261-7 (1998).

Sukhikh et al. "Disorders in cytokine gene expression in endometrial hyperplasia and effect of hormone therapy." Bull Exp Biol Med. Feb. 2005;139(2):235-7.

Talwar "Vaccines for control of fertility and hormome-dependent cancers" Immunol Cell Biol 75(2):184-9 (1997).

Thiess et al. "Tumor necrosis factor (TNF) alpha increases collagen accumulation and proliferation in intestinal myofibroblasts via TNF receptor 2." J Biol Chem. Oct. 28, 2005;280(43):36099-109. Epub Sep. 1, 2005.

Wajant et al. "Tumor necrosis factor signaling." Cell Death Differ. Jan. 10, 2003(1):45-65.

Wozel "Etanercept. An effective TNF alpha-antagonist in the treatment of psoriatic arthritis and chronic plaque psoriasis" Hautarzt. Sep. 2005;56(9):819-30.

Office Action (U.S. Appl. No. 09/083,307; U.S. Patent No. 6,620,382), mailed May 18, 1999.

Reply to Office Action (U.S. Appl. No. 09/083,307; U.S. Patent No. 6,620,382), filed Sep. 23, 1999.

Office Action (U.S. Appl. No. 09/083,307; U.S. Patent No. 6,620,382), mailed Jan. 4, 2000.

Reply to Office Action (U.S. Appl. No. 09/083,307; U.S. Patent No. 6,620,382), filed Apr. 4, 2000.

Appeal Brief (U.S. Appl. No. 09/083,307; U.S. Patent No. 6,620,382), filed Jul. 18, 2000.

Examiner's Answer (U.S. Appl. No. 09/083,307; U.S. Patent No. 6,620,382), mailed Oct. 2, 2000.

Reply Brief (U.S. Appl. No. 09/083,307; U.S. Patent No. 6,620,382), filed Dec. 11, 2000.

Decision on Appeal (U.S. Appl. No. 09/083,307; U.S. Patent No. 6,620,382), mailed Feb. 12, 2002.

Reply to Office Action (U.S. Appl. No. 09/083,307; U.S. Patent No. 6,620,382), filed Jun. 6, 2002.

Appeal Brief (U.S. Appl. No. 09/083,307; U.S. Patent No. 6,620,382), filed Jan. 31, 2003.

Office Action (U.S. Appl. No. 09/316,226; U.S. Patent No. 6,231,536), mailed Feb. 14, 2000.

Reply to Office Action (U.S. Appl. No. 09/316,226; U.S. Patent No. 6,231,536), filed Jun. 14, 2000.

Office Action (U.S. Appl. No. 09/316,226; U.S. Patent No. 6,231,536), mailed Sep. 28, 2000.

Reply to Office Action (U.S. Appl. No. 09/316,226 U.S. Patent No. 6,231,536), filed Nov. 30, 2000.

Interview Summary (U.S. Appl. No. 09/316,226; U.S. Patent No. 6,231,536), mailed Dec. 28, 2000.

Notice of Allowability (U.S. Appl. No. 09/316,226; U.S. Patent No. 6,231,536), mailed Jan. 9, 2001.

Office Action (U.S. Appl. No. 09/709,045), mailed Oct. 22, 2002.

Reply to Office Action (U.S. Appl. No. 09/709,045), filed Apr. 23, 2003.

Office Action (U.S. Appl. No. 09/709,045), mailed Jul. 29, 2003.

Reply to Office Action (U.S. Appl. No. 09/709,045), filed Oct. 30, 2003.

Interview Summary (U.S. Appl. No. 09/709,045), mailed Jul. 12, 2004.

Interview Summary (U.S. Appl. No. 09/709,045), mailed Jan. 11, 2005.

Advisory Action (U.S. Appl. No. 09/709,045), mailed Jul. 6, 2005.

Interview Summary (U.S. Appl. No. 09/709,045), mailed Dec. 23, 2005.

Interview Summary (U.S. Appl. No. 09/709,045), mailed Jan. 4, 2006.

Office Action (U.S. Appl. No. 11/153,524), mailed May 13, 2008.

Reply to Office Action (U.S. Appl. No. 11/153,524), filed Sep. 12, 2008.

Office Action (U.S. Appl. No. 11/153,524), mailed Dec. 17, 2008.

Reply to Office Action (U.S. Appl. No. 11/153,524), filed Mar. 17, 2009.

Advisory Action (U.S. Appl. No. 11/153,524), mailed Mar. 30, 2009.

Office Action (U.S. Appl. No. 11/153,524), mailed Jun. 16, 2009.

Interview Summary (U.S. Appl. No. 11/153,524), mailed Sep. 16, 2009.

Office Action (U.S. Appl. No. 11/929,540), mailed Jul. 2, 2008.

Reply to Office Action (U.S. Appl. No. 11/929,540), filed Nov. 3, 2008.

Office Action (U.S. Appl. No. 11/929,540), mailed Feb. 24, 2009.

Reply to Office Action (U.S. Appl. No. 11/929,540), filed Mar. 12, 2009.

Interview Summary (U.S. Appl. No. 11/929,540), mailed Mar. 13, 2009.

Office Action (U.S. Appl. No. 11/929,540), mailed Jul. 6, 2009.

Reply to Office Action (U.S. Appl. No. 11/929,540), filed Jan. 6, 2010.

Office Action (U.S. Appl. No. 11/929,540), mailed Feb. 17, 2010.

Office Action (U.S. Appl. No. 11/119,214), mailed Jun. 26, 2008.

Reply to Office Action (U.S. Appl. No. 11/119,214), filed Oct. 2, 2008.

Office Action (U.S. Appl. No. 11/119,214), mailed Jan. 8, 2009.

Interview Summary (U.S. Appl. No. 11/119,214), mailed Mar. 13, 2009.

Reply to Office Action (U.S. Appl. No. 11/119,214), Mar. 26, 2009.
Office Action (U.S. Appl. No. 11/119,214), mailed Apr. 6, 2009.
Interview Summary (U.S. Appl. No. 11/119,214), mailed Apr. 13, 2009.

Reply to Office Action (U.S. Appl. No. 11/119,214), filed Jun. 12, 2009.
Office Action (U.S. Appl. No. 11/119,214), mailed Sep. 28, 2009.

* cited by examiner

METHOD AND COMPOSITIONS FOR TREATMENT OF CANCERS

This application is a continuation of U.S. Ser. No. 09/316,226 filed May 21, 1999 now U.S. Pat. No. 6,231,536, which is a continuation-in-part of U.S. Ser. No. 09/083,307 filed May 22, 1998 now U.S. Pat. No. 6,620,382.

BACKGROUND OF THE INVENTION

The present invention is generally in the field of enhancing an immune response, and particularly relates to the removal of inhibitors of immune mediators, in combination with anti-angiogenic compounds, cytokines, compounds inducing a procoagulant state, chemotherapeutics and/or radiation.

Conventional cancer therapy is based on the use of drugs and/or radiation which kills replicating cells, hopefully faster than the agents kill the patient's normal cells. Surgery is used to reduce tumor bulk, but has little impact once the cancer has metastasized. Radiation is effective only in a localized area.

The treatments can in themselves kill the patient, in the absence of maintenance therapy. For example, for some types of cancer, bone marrow transplants have been used to maintain the patient following treatment with otherwise fatal amounts of chemotherapy. Efficacy has not been proven for treatment of solid tumors, however. "Cocktails" of different chemotherapeutic agents and combinations of very high doses of chemotherapy with restorative agents, for example, granulocyte macrophage colony stimulating factor ("GM-CSF"), erythropoietin, thrombopoetin granulocyte stimulating factor, ("G-CSF"), macrophage colony stimulating factor ("M-CSF") and stem cell factor ("SCF") to restore platelet and white cell levels, have been used to treat aggressive cancers. Even with the supportive or restrictive therapy, side effects are severe.

Other treatments have been tried in an attempt to improve mortality and morbidity. Vaccines to stimulate the patient's immune system have been attempted, but not with great success. Various cytokines, alone or in combination, such as tumor necrosis factor, interferon gamma, and interleukin-2 ("IL-2") have been used to kill cancers, but have not produced cures. More recently, anti-angiogenic compounds such as thalidomide have been tried in compassionate use cases and shown to cause tumor remission. In animal studies, compounds inducing a procoagulant state, such as an inhibitor of protein C, have been used to cause tumor remission. New studies have shown that inhibitors of cytokine receptors, such as tumor necrosis factor receptors ("TNF-Rs") which are released in a soluble form from tumor cells, in high concentrations relative to normal cells, may restore the immune system's attack on the tumor cells (Jablonska and Peitruska, Arch. Immunol. Ther. Exp. (Warsz) 1997, 45(5-6), 449-453; Chen, et al., J. Neuropathol. Exp. Neurol. 1997, 56(5), 541-550).

U.S. Pat. No. 4,708,713 to Lentz describes an alternative method for treating cancer, involving ultrapheresis to remove compounds based on molecular weight, which promotes an immune attack on the tumors by the patient's own white cells.

Despite all of these efforts, many patients die from cancer; others are terribly mutilated. It is unlikely that any one therapy will be effective to cure all types of cancer.

It is therefore an object of the present invention to provide a method and compositions for treatment of solid tumors.

It is a further object of the present invention to provide a method and composition that does not involve non-selective, extremely toxic, systemic chemotherapy.

SUMMARY OF THE INVENTION

A method to treat cancer uses ultrapheresis, refined to remove compounds of less than 120,000 daltons molecular weight, followed by administration of replacement fluid, to stimulate the patient's immune system to attack solid tumors. In the preferred embodiment, the patient is ultrapheresed using a capillary tube ultrafilter or parallel plate filter having a molecular weight cutoff of 120,000 daltons, sufficient to filter at least one blood volume. The preferred replacement fluid is ultrapheresed normal plasma. Alternatively, the patient is pheresed to selectively remove soluble receptor/inhibitors to soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), or soluble interferon-gamma receptor ("sIFN-gammaR"). These can be removed by binding to the cytokine, an epitope thereof, or an antibody to the receptor. These can be immobilized in the filter, in a column, or using other standard techniques for binding reactions to remove proteins from the blood or plasma of a patient. The patient is preferably treated daily for three weeks, diagnostic tests conducted to verify that there has been shrinkage of the tumors, then the treatment regime is repeated.

The treatment is preferably combined with an alternative therapy, for example, treatment with an anti-angiogenic compound, one or more cytokines such as TNF, gamma interferon, other interferons, or IL-2, or a procoagulant compound. The treatment increases the inflammation against tumors by allowing cytokines, such as TNF, to work effectively. This provides a basis for an improved effect when combined with any treatment that enhances cytokine activity against the tumors, for example, treatments using alkylating agents, doxyrubicin, carboplatinum, cisplatinum, cistplatimum, and taxol, and other drugs which may be synergistic in effect with "unblocked" cytokines. Alternatively, the ultrapheresis treatment can be combined with local chemotherapy, systemic chemotherapy, and/or radiation.

DETAILED DESCRIPTION OF THE INVENTION

Figure 1:
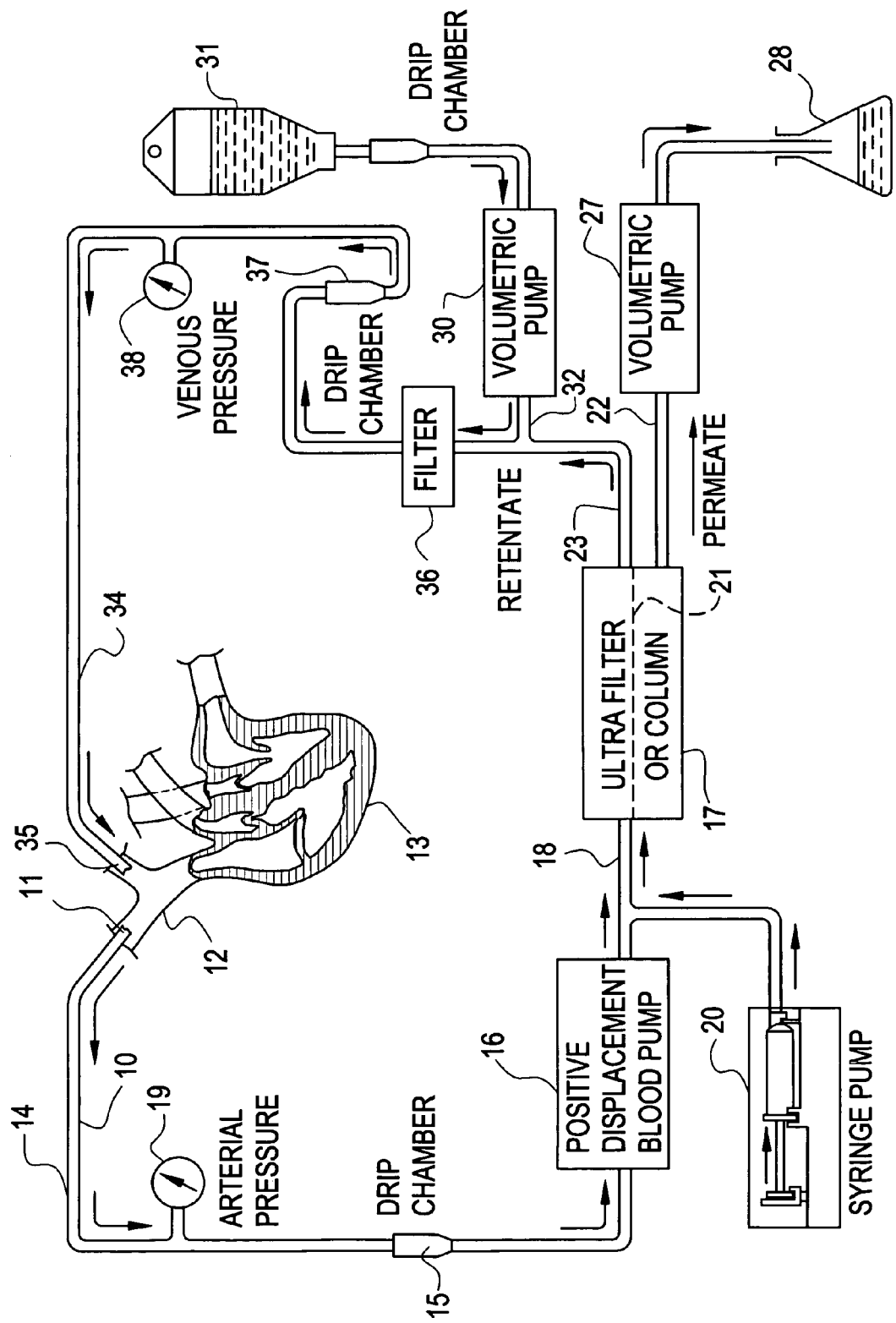
FIGS. 1 and 2 are schematics of the system for ultrapheresis.

The methods and devices disclosed herein are useful treatment of patients with cancer, immune-mediated disorders, chronic parasitism, some viral diseases, and other disorders characterized by elevated levels of TNF receptors or inhibitors to IL-2, IL-6, gamma interferon, or other pro-inflammatory signals as well as white cell activation. Examples demonstrate efficacy in treating cancer patients.

I. Ultrapheresis

A. Ultrapheresis System

1. Filters

The filter must be biocompatible, and suitable for contact with blood, without causing excessive activation of platelets or clotting. Devices will typically be either parallel plate filters or capillary membrane filters. These can be adapted from devices currently in use for kidney dialysis. The capillary membrane filters will typically have a surface area of between about 0.25 and 1 m² for use with children and between about 1 and 3 m² for use with adults. The parallel plate filters will typically have a surface area in the range from 0.1 and 2 cm²/ml of blood to be filtered.

The filter membranes will typically be a biocompatible or inert thermoplastic such as polycarbonate, polytetrafluoroethylene (Teflon®), polypropylene, ethylene polyvinyl alcohol or polysulfone, having a pore size typically of between 0.02 and 0.05 microns in a capillary membrane filter and of between 0.04 and 0.08 microns in a parallel plate filter. The actual pore size that yields the desired cutoff of approximately 120,000 daltons is determined based on the fluid flow geometry, shear forces, flow rates, and surface area. The effective cutoff for a capillary membrane filter with a pore size of 0.03 microns is 120,000 daltons, with a sieving coefficient of between 10 and 30%. This results in only a trivial amount of IgG being removed from the patient's blood. The filter membrane should be less than about 25 microns, preferably less than about 10 microns, thick. The permeable membrane should not cause blood clotting or otherwise react with the blood.

A preferred membrane is one in which the pores are made by electron beams directed perpendicularly to the surface because the size and density of the pores can be accurately controlled in this manner. The pores are essentially circular in cross section so the effective pore size is the actual pore size. The effective pore size of ultrafiltered media having pores with non-circular cross sections shall be the diameter of a circular pore which will pass molecules or other components of an equivalent size to the molecules or other components which pass through the filter medium in question.

Suitable devices can be obtained from Asahi Chemical Company, Japan, and Kuraray Co., Ltd, 1-12-39, Umeda, ite-ku, Osaka 530, Japan.

Staged filters can also be used, which have different pore sizes and/or geometries or surface areas, to provide for a "staggered" removal of materials from the blood. Alternatively, although not at this time preferred, one can use differential centrifugation, to provide for an appropriate separation of blood components. Specific absorbing columns can also be employed to selectively remove specific cytokine and cellular inhibitors from the filtered plasma so that the ultrafiltrate (treated plasma) can be returned to the patient.

2. Process Controls and Fluid Handling

The patient will typically be connected to the blood processing device using standard intravenous tubing, with connections similar to those used for plateletpheresis, so that blood can be removed from the patient at one site and returned at another. The tubing is connected to a pump that controls the flow rate so that in the preferred embodiment one blood volume (based on approximately 7% of the total body weight) is processed over a period of approximately 2½ hours. The filtrate is then returned from the filtration device to the patient at the second site. Standard microprocessor controls can be used to regulate the blood flow, for example, by monitoring the volume of the blood products being removed, in combination with flow rate monitors and pump speed.

The entire system should first be flushed with saline and then treated with an anticoagulant or anticlotting agent, such as sodium heparin, to be sure that there are no locations within the system where blood clotting can occur. Moreover, small amounts of anticoagulants should be continually introduced into the blood stream directed to the ultrafilter to ensure than no clotting occurs during the filtration process. All of the surfaces of the system which come in contact with the blood and fluids which are infused into the patient must be sterilized prior to commencing treatment.

FIG. 1 illustrates a system for ultrapheresis. Blood is removed from a patient by means of a venous catheter 10 with the distal lead 11 thereof disposed in the superior vena cava 12 leading to the patient's heart 13. The blood passes through conduit 14 to a drip chamber 15 and then into pump 16 which controls the pressure of the blood to the separation unit 17, preferably an ultrafilter as shown, through conduit 18. A pressure gauge 19 is provided on conduit 14 to continually monitor arterial pressure. A syringe pump 20 feeds an anti-clotting drug such as sodium heparin to conduit 18 to prevent the clotting of blood in the ultrafilter 17. In the ultrafilter 17 the blood stream passes over the ultrafilter medium or membrane or absorbent column 21 under pressure. The blood fraction including the low molecular weight components passes through the membrane or absorbent column 21 and is discharged as permeate through conduit 22. The retentate or treated blood containing the high molecular weight components, which include whole blood cells and platelets, is discharged into conduit 23 which ultimately leads back to the patient. Volumetric pump 27 passes a controlled amount of permeate to a container 28 for containment and for measuring. Volumetric pump 30, which is preferably the same type and capacity as pump 27, pumps replacement fluid from a container 31 to conduit 32, which directs the fluid to conduit 23 where it mixes with the retentate or treated blood. The treated blood and other components are returned to the patient through venous catheter 34, the distal or discharge end of which is disposed in the brachiocephalic vein. The volumetric pumps 27 and 30 are preferably set either to pump the same total amount of fluid or to pump at the same rate, so that the same volume of fluid which is removed from the patient's blood stream as permeate is returned as replacement fluid. The blood stream in conduit 23 is passed through filter 36 to remove clots or other debris from the blood stream. A drip chamber 37 ensures that no significant quantities of air enter the patient's blood stream. A venous pressure gauge 38 is provided to continually monitor venous blood pressure.

Figure 2:
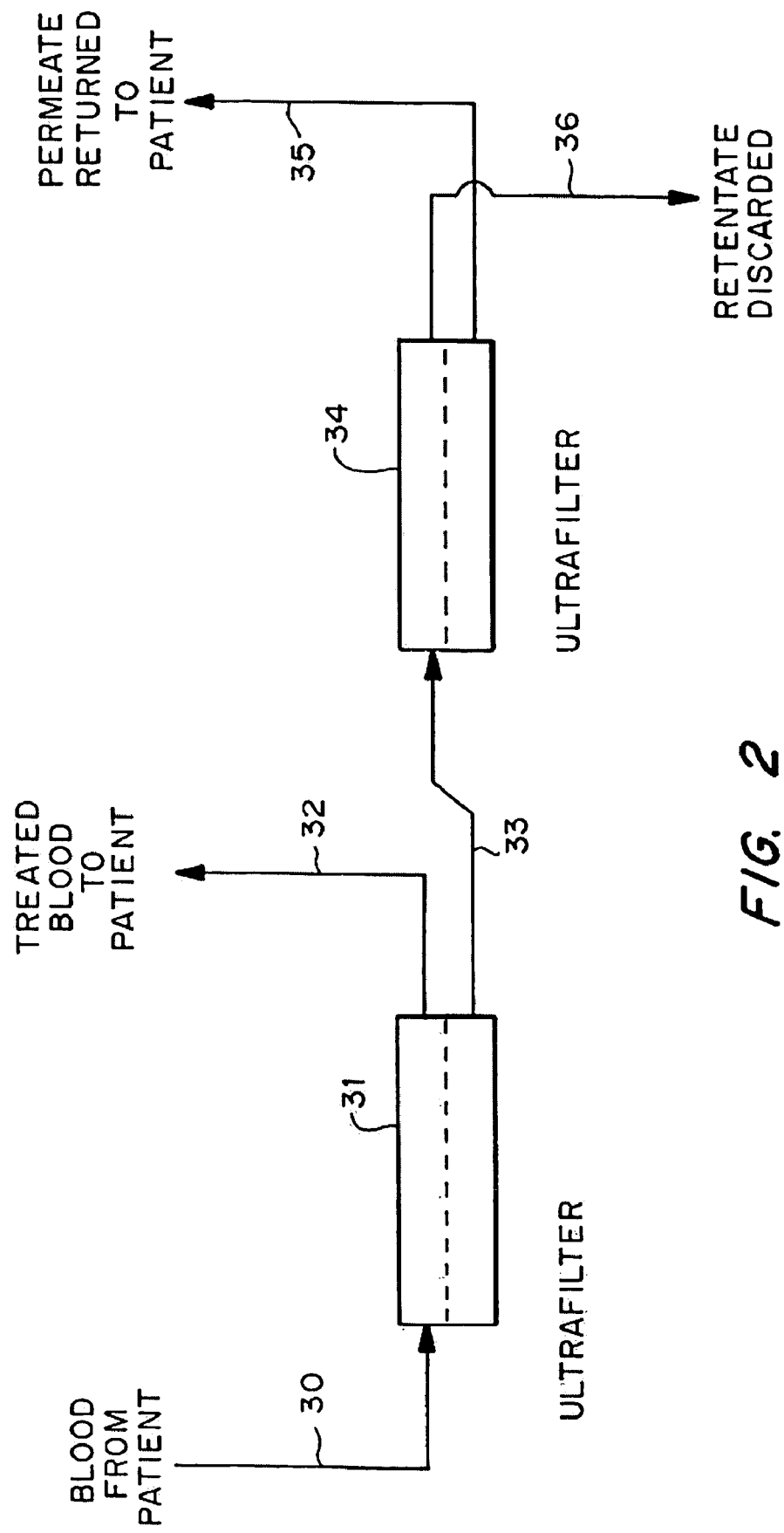

FIG. 2 illustrates another embodiment wherein blood removed from a patient is first passed through conduit 30 to a first ultrafilter 31 to selectively separate a blood fraction with components having molecular weights less than about 1,000,000 Daltons. The retentate from this ultrafiltration which contains the high molecular weight components is returned through conduit 32 to the patient. The permeate from the first ultrafilter 31 is passed through conduit 33 to a second ultrafilter 34 where a blood fraction having a molecular weight below 30,000 is removed from the permeate stream from the first ultrafilter 31. The permeate from the second ultrafilter 34, which contains the very low molecular weight components such as salts and nutrients may be returned to the patient through conduit 35. The retentate from the second ultrafilter which contains blocking factors, IgG immunoglobulins and other components is discharged through conduit 36.

Blood should be pumped through the ultrafilter unit at sufficient pressure to cause the blood components having the immunosuppressive effects to pass through the filter but at a velocity which will not excessively shear or otherwise damage the blood cells passing over the membrane. Generally it has been found that the ratio of the area of the membrane to the amount of blood treated per hour should be within about 0.1 to 2 cm/mL. Differential pressure across the membrane should range from about 2 to 20 mM Hg.

3. Replacement Fluids

The patient must receive replacement fluids following filtration. The preferred replacement fluid is ultrapheresis normal plasma, for example, expired plasma obtained from the Red Cross, which has been filtered using the same filter as used to treat the patient. Alternatively, the patient can be administered normal albumin, or fresh frozen plasma diluted with saline.

II. Treatment With Adjuvant Therapies

Standard ultrapheresis is conducted over a period of time until a positive indication is observed. This is typically based on diagnostic tests which show that there has been some reduction in tumor size or which suggests tumor inflammation. The patient is preferably treated daily for three weeks, diagnostic tests conducted to verify that there has been shrinkage of the tumors and/or inflammation, then the treatment regime is repeated.

Surgical (or vacuum) removal of necrotic material may be required prior to or during treatment to avoid toxicity associated with high tumor burden.

This procedure has been demonstrated to cause a significant response (greater than 50% reduction in size of tumors) in a variety of solid tumors in approximately 50% of patients who have failed all other treatment modalities. A tumor specific inflammatory response provoked by ultrapheresis has been documented in approximately 75% of patients in metastatic melanoma clinical trials. This inflammation is characterized by redness, swelling, warmth, and tenderness and is confined to tumors only. There has been no associated injury to non-cancerous tissue. This tumor specific inflammatory response has led to a 50% or greater reduction in the size of tumors in 50% of patients studied so far. Clinical trials have also demonstrated a 44% major reduction of tumor metastases in human breast cancer and prostate cancer.

Tumor specific inflammation has been observed in patients with metastatic colon cancer, ovarian cancer, lung cancer, head and neck cancer, cervical and endometrial cancers. In some cases, this inflammation has been followed by significant tumor regressions in each tumor type. The significance of response in such diverse tumor types strongly suggests that ultrapheresis modifies the patient's response to the tumor in favor of successful immunologic control of the tumor. Types of tumors that are particularly sensitive to the ultrapheresis include epithelial tumors, sarcomas, melanomas and glioblatomas.

It would clearly be advantageous to cause complete remissions. Based on the presumed mechanism that the process is removing immune inhibitors produced by the tumors, especially inhibitors of cytokines and other immune mediators, it is possible to treat the patients with adjuvant or combination therapies, that enhance the results achieved with the ultrapheresis. TNF-alpha and beta receptors are thought to be particularly important immune inhibitors. Therefore, compounds which enhance TNF activity are particularly preferred. These include anti-angiogenic compounds, such as thalidomide, procoagulant compounds, cytokines and other immunostimulants. Standard chemotherapeutic agents and/ or radiation can also be used with the ultrapheresis.

A. Anti-Angiogenic Compounds

Any anti-angiogenic compound can be used. Exemplary anti-angiogenic compounds include O-substituted fumagillol and derivatives thereof, such as TNP-470, described in U.S. Pat. Nos. 5,135,919, 5,698,586, and 5,290,807 to Kishimoto, et al.; angiostatin and endostatin, described in U.S. Pat. Nos. 5,290,807, 5,639,725 and 5,733,876 to O'Reilly; thalidomide, as described in U.S. Pat. Nos. 5,629,327 and 5,712,291 to D'Amato; and other compounds, such as the anti-invasive factor, retinoic acid, and paclitaxel, described in U.S. Pat. No. 5,716,981 to Hunter, et al., and the metalloproteinase inhibitors described in U.S. Pat. No. 5,713,491 to Murphy, et al. Thalidomide is administered once daily, 200 mg orally.

B. Procoagulant Compounds

Protein C is a vitamin K-dependent plasma protein zymogen to a serine protease. Upon activation it becomes a potent anticoagulant. Activated protein C acts through the specific proteolysis of the procoagulant cofactors, factor VIIIa and factor Va. This activity requires the presence of another vitamin K-dependent protein, protein S, calcium and a phospholipid (presumably cellular) surface. As described in *Hemostatsis and Thrombosis: Basic Principles and Clinical Practice* 2nd Ed., Colman, R. W., et al.,p. 263 (J. B. Lippincott, Philadelphia, Pa. 1987), protein C circulates in a two-chain form, with the larger, heavy chain bound to the smaller light chain through a single disulfide link. Protein C is activated to activated protein C (APC). Thrombin is capable of activating protein C by the specific cleavage of the $Arg^{12}$-$Leu^{13}$ bond in the heavy chain. In vivo, in the presence of physiological concentrations of calcium, the rate of this activation is enhanced dramatically when thrombin is bound to the endothelial cell cofactor, thrombomodulin. Matschiner, et al., *Current Advances in Vitamin K Research,* pp. 135-140, John W. Suttie, ed. (Elsevier Science Publishing Co., Inc. 1988) have further reviewed the role of the Vitamin K dependent proteins in coagulation.

Blockage of the natural anticoagulant pathways, in particular the protein C pathway, uses the natural procoagulant properties of the tumor to target the tumor capillaries for microvascular thrombosis, leading to hemorrhagic necrosis of the tumor, as described in U.S. Pat. No. 5,147,638 to Esmon, et al. Examples of such compounds include anti-protein C and anti-protein S.

C. Cytokines

The biologic activity and clinical effectiveness of pro-inflammatory cytokines is augmented by ultrapheresis in the patient with cancer and other states of acquired immune tolerance. Specifically, both TNF alpha and TNF beta, in doses of between approximately 100 to 500 micrograms per meter squared body surface area (M2BSA), can enhance the immune reaction in aggressive tumors. Monocyte and lymphocyte activation is augmented by INF-alpha, INF-beta and gamma. The IL-1 and IL-2 receptor antagonists are removed by ultrapheresis and thereby upregulate the in vivo activity of these cytokines. An 80 kD glycoprotein, which is responsible for inhibiting blastoid transformation in advanced malignancy, chronic infectious disease and pregnancy, has recently been found, and appears to be responsible for the loss of delayed hypersensitivity reactions in these diseases, which is removed by this process. This is significant because in removing this type of suppression, vaccines of all types will work better. Dosage regimes for IFN-alpha and beta are 3 M units subcutaneous three times a week up to 20 M units/M2 BSA daily. Interferon-gamma is administered in a dosage of between 100 to 1000 micgms per day.

D. Anti-Cytokine Receptor Molecules

It is well established that TNF receptor 1 and TNF receptor 2 molecules are shed by tumor cells, and that these molecules appear to inhibit immune mediated attack by the host on the tumor cells. The ultrapheresis is believed to remove the majority of these soluble receptors. Additional, and/or selective, removal of these soluble receptor/inhibitors to soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), or soluble interferon-gamma receptor ("sIFN-gammaR") can be used to supplement or instead of the ultrapheresis. The advantage of selective removal is that the same beneficial effect is obtained in treatment of the disorder but the treatment is much less expensive and safer since exogenous plasma or albumin does not have to be administered to the patient when there is selective removal. These can be removed by binding to the cytokine, an epitope thereof, or an antibody to the receptor. These can be immobilized in the filter, in a column, or using other standard techniques for binding reactions to remove proteins from the blood or plasma of a patient. As used herein, antibody refers to antibody, or antibody fragments (single chain, recombinant, or humanized), immunoreactive against the receptor molecules. In the preferred embodiment, these antibodies are immobilized on the ultrapheresis membrane filters, using standard antibody coupling techniques. In the most preferred embodiment, the antibody is reactive with the carboxy-terminus of the shed receptor molecules, thereby avoid concerns with signal transduction by the receptor is still present on the cell surface.

E. Chemotherapeutic Agents

Preferred chemotherapeutic agents are those which are synergistic with TNF, for example, alkylating agents, doxyrubicin, carboplatinum, cisplatinum, and tomoxifen. Tomoxifen plays a role not only in blocking of estrogen receptors but also certain growth factor receptors such as epidermal derived growth factor ("EDGF"), fibroblast derived growth factor ("FDGF"), tumor derived growth factor ("TDGF"), TDGF-β and platelet derived growth factor ("PDGF") and therefore may be complementary to inflammation against cancers provoked by ultrapheresis.

F. Radiation

Radiation therapy is destructive of normal tissue, causing tumors to die partially by an inflammatory attack. Ultrapheresis allows the use of lower doses of radiation to kill residual tumor cells and spare normal tissue. In a preferred method, ultrapheresis is used as the initial therapy, followed by radiation at approximately one-half of the normal dosages. It is well established that TNF kills tumor cells by generating free oxygen radicals, hydroxyl radicals and halide ions, and that radiation therapy generates carbonium ions in tissue. Therefore the combination of the two is more effective in killing cancer cells than either alone.

III. EXAMPLES

Example 1

Treatment of a Patient with Metastatic Leiomyoscarcoma with Ultrapheresis

Mrs. J. K. is a 43 year old lady with metastatic leiomyoscarcoma with six (6) lung metastases all of which developed within one month of surgery on both lungs to remove tumors. These tumors had also failed methotrexate, adriamycin, ifosphomide, and dactinomycin.

She received 24 ultrapheresis procedures with no side effects. One month later, CAT scan revealed only four (4) tumors and these were reduced in size by 50%.

Example 2

Treatment of Patients with Breast Cancer by Ultrapheresis and Thalidomide

Mrs. J. R. is a 44 year old lady who had metastatic breast cancer that had failed radiation therapy and treatment with chemotherapeutic agents: cytoxan, adriamycin, 5-FU, taxol, cis-platin, navalbine, tamoxofin and arimedex. Tumor at the time of ultrapheresis was documented in lungs, bone and skin of the entire left anterior and lateral chest.

She was treated with 15 ultrapheresis procedures over a three week period. She experienced marked inflammation in the tumors of his skin, increased pain from the tumors in her bones, and swelling of the tumors in her lungs. She then received the drug thalidomide 200 mg at night. The redness and swelling in her skin improved within 2 days and her breathing returned to normal within one week. Two weeks after completing treatment, all tumor in her skin had resolved clinically, her bone pain resolved and the tumors in her lungs resolved on repeat CAT scan. One week later, she returned to work as a school counselor. She tested disease free two months after treatment and was being maintained on thalidomide at the same dose.

Example 3

Treatment of Patient with Metastic Melanoma with Ultrapheresis and Thalidomide

Mr. P. G. is a 54 year old engineer with metastatic melanoma with metastases to lung and to lymph nodes in the mediastinum.

He received 24 ultrapheresis procedures, resulting in a 25% reduction of tumors. He was subsequently treated with an additional 12 procedures, resulting in minor tumor reduction despite evidence of tumor inflammation. The tumors regrew within one month. He was again retreated with ultrapheresis, again resulting in inflammation and some minor regression, but was then treated with thalidomide at the time of tumor inflammation. Two months later, repeat CAT scan showed complete disappearance of tumors in the lung and mediastinum. He is being followed closely and shows no evidence of disease and has no medical complaints six months after completing treatment.

Example 4

Treatment of a Patient with Metastic Adenocarcinoma with Ultrapheresis and Thalidomide Dr. R. S. is a 59 year old gentlemen with metastatic adenocarcinoma of the left upper lung with metastases to liver, brain and bones. His tumors had failed to respond to taxol, cisplatin and etoposide. His brain tumors had responded to radiation therapy., He received 15 ultrapheresis procedures. Each procedure caused increased pain in tumors of his spine, pelvis, right hip and left shoulder. Follow up scans after ultrapheresis treatment revealed resolution of tumors in pelvis, spine, hip, and ribs. There was a 50% reduction in the primary tumor in the lung and liver. Thalidomide was then started at 200 mg each night. One month later, the scans revealed further reduction in the tumors in lung and liver. The patient's pains have all been resolved and he is asymptomatic at this time.

Modifications and variations of the method and compositions described herein will be obvious to those skilled in the art. Such modifications and variations are intended to come within the scope of the appended claims.

I claim:

1. A method for inducing an immune response against transformed, infected or diseased tissue in a patient comprising selectively removing soluble cytokine receptor molecules selected from the group consisting of soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), and soluble interferon-gamma receptor ("sIFN-gammaR") from blood, plasma, or one or more components of the blood of the patient until the transformed, infected, or diseased tissue is reduced in size or is inflamed.

2. The method of claim 1 wherein the tissue is a solid tumor.

3. The method of claim 1 wherein the components are removed from one blood volume.

4. The method of claim 1 wherein the components are removed in multiple treatments.

5. The method of claim 1 further comprising treating the tissue with an agent selected from the group consisting of anti-angiogenic compounds, procoagulant compounds, cytokines, chemotherapeutic agents, and radiation.

6. The method of claim 5 wherein the agent is a cytokine and the cytokine is selected from the group consisting of GM-CSF, erythropoietin, thrombopoetin, G-CSF, M-CSF and SCF.

7. The method of claim 1 wherein the soluble cytokine receptor molecules are selected from the group consisting of soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), and soluble interferon-gamma receptor ("sIFN-gammaR").

8. The method of claim 1 wherein the cytokine receptor molecules are removed by binding to the cytokine or to an antibody or antibody fragment immunoreactive with the cytokine receptor molecules.

9. The method of claim 8 wherein the cytokine or antibody or antibody fragments are immobilized in a filter or column through which the patient's blood or plasma is circulated prior to being returned to the patient.

10. The method of claim 1 wherein the soluble cytokine receptor molecule is soluble tissue necrosis factor receptor-1 ("sTNFR-1").

11. The method of claim 1 wherein the soluble cytokine receptor molecule is soluble tissue necrosis factor receptor-2 ("sTNFR-2").

12. The method of claim 1 wherein the soluble cytokine receptor molecule is soluble interleukin-2 receptor ("sIL-2R").

13. The method of claim 1 wherein the soluble cytokine receptor molecule is soluble interleukin-1 receptor ("sIL-1R").

14. The method of claim 1 wherein the soluble cytokine receptor molecule is soluble interleukin-6 receptor ("sIL-6R").

15. The method of claim 1 wherein the soluble cytokine receptor molecule is soluble interferon-gamma receptor ("sIFN-gammaR").

* * * * *